United States Patent
Jackson et al.

(10) Patent No.: US 12,004,938 B2
(45) Date of Patent: Jun. 11, 2024

(54) FLOW MODIFYING IMPLANTS

(71) Applicant: Shockwave Medical, Inc., Santa Clara, CA (US)

(72) Inventors: Keith Alan Jackson, Brooker, FL (US); Shmuel Banai, Tel Aviv (IL); Colin Alexander Nyuli, Vancouver (CA); Elliot Y. K. Hong, Vancouver (CA)

(73) Assignee: SHOCKWAVE MEDICAL, INC., Santa Clara, CA (US)

( * ) Notice: Subject to any disclaimer, the term of this patent is extended or adjusted under 35 U.S.C. 154(b) by 124 days.

(21) Appl. No.: 16/751,860

(22) Filed: Jan. 24, 2020

(65) Prior Publication Data

US 2020/0237495 A1    Jul. 30, 2020

Related U.S. Application Data

(60) Provisional application No. 62/796,348, filed on Jan. 24, 2019.

(51) Int. Cl.
*A61F 2/06*    (2013.01)
*A61F 2/90*    (2013.01)
(Continued)

(52) U.S. Cl.
CPC .................. *A61F 2/06* (2013.01); *A61F 2/90* (2013.01); *A61F 2/958* (2013.01);
(Continued)

(58) Field of Classification Search
CPC .... A61F 2/06; A61F 2/90; A61F 2/958; A61F 2002/0081; A61F 2002/821; A61F 2210/0014; A61F 2220/0008; A61F 2230/0006; A61F 2230/0008; A61F 2230/0065; A61F 2230/0067;
(Continued)

(56) References Cited

U.S. PATENT DOCUMENTS 5,575,818 A    11/1996  Pinchuk
5,769,884 A *  6/1998  Solovay .................... A61F 2/07
                                                        606/194
(Continued)

FOREIGN PATENT DOCUMENTS

FR        2676355 A1    11/1992
WO    WO-2012015825 A2    2/2012
(Continued)

OTHER PUBLICATIONS

"International Application Serial No. PCT/US2020/015053, International Search Report dated Jun. 2, 2020", 4 pgs.
(Continued)

*Primary Examiner* — Suzette J Gherbi
(74) *Attorney, Agent, or Firm* — Morrison & Foerster LLP

(57) ABSTRACT

Described herein are devices, systems, and methods for modifying blood flow and improving tissue oxygenation in an individual. More specifically, described herein are flow modifying implants, delivery systems, and methods of treatment using flow modifying implants. Also described herein are methods for preventing reperfusion injury in an individual using a flow modifying implant to prevent the reperfusion injury.

38 Claims, 15 Drawing Sheets

(51) Int. Cl.
*A61F 2/958* (2013.01)
*A61F 2/00* (2006.01)
*A61F 2/82* (2013.01)

(52) U.S. Cl.
CPC . *A61F 2002/0081* (2013.01); *A61F 2002/821* (2013.01); *A61F 2210/0014* (2013.01); *A61F 2220/0008* (2013.01); *A61F 2230/0006* (2013.01); *A61F 2230/0008* (2013.01); *A61F 2230/0065* (2013.01); *A61F 2230/0067* (2013.01); *A61F 2230/0069* (2013.01); *A61F 2230/0084* (2013.01); *A61F 2250/0018* (2013.01); *A61F 2250/0024* (2013.01); *A61F 2250/0048* (2013.01)

(58) Field of Classification Search
CPC ...... A61F 2230/0069; A61F 2230/0084; A61F 2250/0018; A61F 2250/0024; A61F 2250/0048; A61F 2250/0039; A61F 2002/068
See application file for complete search history.

(56) References Cited

U.S. PATENT DOCUMENTS

| | | | |
|---|---|---|---|
| 7,914,568 B2* | 3/2011 | Cully | A61F 2/07 623/1.13 |
| 9,301,870 B2* | 4/2016 | Shelton | A61F 5/453 |
| 10,045,877 B2* | 8/2018 | Weig | A61F 5/445 |
| 10,098,739 B2* | 10/2018 | McKinnis | A61F 2/2475 |
| 10,307,242 B2* | 6/2019 | Walzman | A61F 2/013 |
| 10,478,290 B2* | 11/2019 | Emani | A61F 2/2418 |
| 10,568,731 B2* | 2/2020 | Karavany | A61F 2/07 |
| 10,952,840 B2* | 3/2021 | Walther | A61F 2/90 |
| 10,952,854 B2* | 3/2021 | Heneghan | A61F 2/2418 |
| 11,207,200 B2* | 12/2021 | Karavany | A61F 2/07 |
| 11,291,807 B2* | 4/2022 | Eigler | A61F 2/01 |
| 11,324,619 B1* | 5/2022 | Yacoby | A61F 2/07 |
| 11,439,492 B2* | 9/2022 | Walzman | A61B 17/22 |
| 11,458,287 B2* | 10/2022 | Eigler | A61B 17/12172 |
| 2003/0153943 A1* | 8/2003 | Michael | A61F 2/012 606/200 |
| 2004/0138761 A1* | 7/2004 | Stack | A61F 2/04 623/23.65 |
| 2004/0172141 A1* | 9/2004 | Stack | A61F 2/04 623/23.65 |
| 2005/0010285 A1* | 1/2005 | Lambrecht | A61F 2/2418 623/2.18 |
| 2005/0015112 A1* | 1/2005 | Cohn | A61F 2/2427 623/2.14 |
| 2005/0070993 A1 | 3/2005 | Boekstegers et al. | |
| 2005/0154448 A1* | 7/2005 | Cully | A61F 2/07 623/1.15 |
| 2006/0106450 A1 | 5/2006 | Ben Muvhar | |
| 2009/0125098 A1* | 5/2009 | Chuter | A61F 2/07 623/1.26 |
| 2009/0164000 A1* | 6/2009 | Shirley | A61B 17/12109 623/1.24 |
| 2012/0116498 A1* | 5/2012 | Chuter | A61F 2/2412 623/1.26 |
| 2017/0216025 A1* | 8/2017 | Nitzan | A61F 2/2412 |
| 2017/0296198 A1 | 10/2017 | Rudakov et al. | |
| 2017/0348125 A1 | 12/2017 | Chobotov | |
| 2019/0029798 A1* | 1/2019 | Walther | A61F 2/07 |
| 2020/0229956 A1* | 7/2020 | Jackson | A61F 2/848 |
| 2021/0068993 A1* | 3/2021 | Hebert | A61B 17/12031 |
| 2021/0275188 A1* | 9/2021 | Plaza | A61B 17/12118 |
| 2022/0071788 A1* | 3/2022 | Karavany | A61F 2/06 |
| 2022/0110744 A1* | 4/2022 | Heneghan | A61F 2/2418 |
| 2023/0132996 A1* | 5/2023 | Stefanov | A61B 17/221 606/159 |
| 2023/0157722 A1* | 5/2023 | Wachli | A61B 17/42 600/204 |
| 2023/0255759 A1* | 8/2023 | Chuter | A61F 2/2412 623/1.14 |

FOREIGN PATENT DOCUMENTS

| | | |
|---|---|---|
| WO | WO-2014137830 A1 | 9/2014 |
| WO | WO-2019097424 A2 | 5/2019 |
| WO | WO-2020154661 A1 | 7/2020 |

OTHER PUBLICATIONS

"International Application Serial No. PCT/US2020/015053, Written Opinion dated Jun. 2, 2020", 8 pgs.

"International Application Serial No. PCT US2020 015053, Invitation to Pay Additional Fees mailed Mar. 26, 2020", 2 pgs.

"International Application Serial No. PCT/US2020/015053, International Preliminary Report on Patentability dated Aug. 5, 2021", 11 pgs.

"Australian Application Serial No. 2020211601, Subsequent Examiners Report dated Nov. 2, 2022", 6 pgs.

"Canadian Application Serial No. 3,127,757, Examiner's Rule 86(2) Report dated Nov. 23, 2022", 6 pgs.

"Australian Application Serial No. 2020211601, First Examination Report dated Jul. 29, 2022", 3 pgs.

"Australian Application Serial No. 2020211601, Response filed Oct. 6, 2022 to First Examination Report dated Jul. 29, 2022", 28 pgs.

"European Application Serial No. 20745788.8, Extended European Search Report dated Sep. 12, 2022", 7 pgs.

"European Application Serial No. 20717429.3, Response to Communication pursuant to Rules 161 and 162 filed Mar. 11, 2022", 10 pgs.

* cited by examiner

FLOW MODIFYING IMPLANTS

CLAIM OF PRIORITY

This patent application claims the benefit of priority of U.S. Provisional Patent Application Ser. No. 62/796,348 filed on Jan. 24, 2019 which is hereby incorporated by reference herein in its entirety.

CROSS-REFERENCE TO RELATED PATENT DOCUMENTS

The present application is related to U.S. Pat. No. 9,364,354; the entire contents of which are incorporated herein by reference.

BACKGROUND

Chronic angina pectoris, refractory to medical and interventional therapies, is a common and disabling medical condition, and a major public health problem that affects millions of patients worldwide. Angina is a clinical symptom of myocardial ischemia, which is insufficient oxygenated blood supply to certain areas of the heart muscle (myocardium).

Refractory angina is common in patients who are not good candidates for revascularization, and also in patients following successful revascularization. The prevalence of angina appears in 25% of patients after 1 year, and up to 45% of patients 3 years following successful or unsuccessful revascularization.

Refractory angina may be the presenting symptom of a wide range of clinical entities, including obstructive coronary artery disease (CAD), microvascular (small vessel) disease with patent epicardial coronary arteries, hypertrophic cardiomyopathy (excessive thickening of the heart muscle), and left ventricular diastolic dysfunction (impaired relaxation of the heart muscle during diastole). In patients with obstructive CAD, refractory angina can be due to any degree of disease severity within the wide spectrum between a single discrete coronary branch occlusion and a diffuse severe CAD.

Chronic angina is associated with an increased risk of both cardiovascular hospitalizations and significant healthcare costs.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

DETAILED DESCRIPTION

Figure 1:
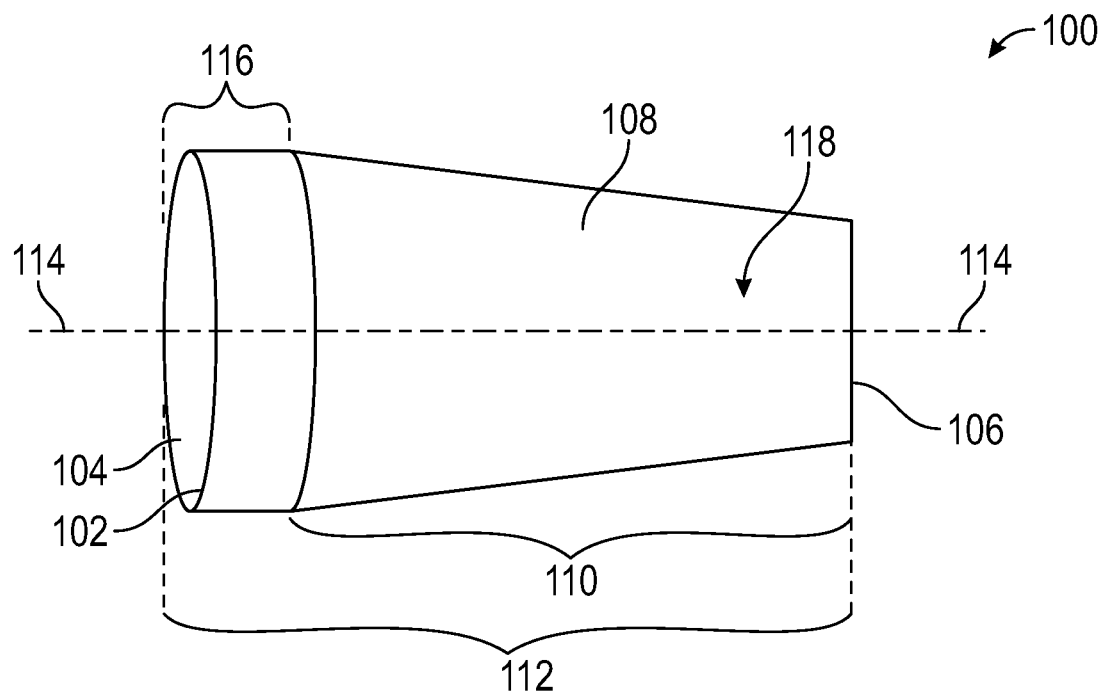
FIG. 1 is a schematic showing a flow modifying implant.

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

Described herein are devices, systems, and methods, for modifying flow of blood or other body fluids to a tissue in a body of an individual. Optionally, in any example, a modified flow of blood or other fluid, caused by the devices, systems, and methods described herein, may result in improved tissue oxygenation or other desirable effect. Optionally, in any example, a modified flow of blood, caused by the methods described herein (examples of which utilize any of the devices and systems described herein), may result in prevention of reperfusion injury.

Devices for Improving Flow of Blood to a Tissue

Described herein are devices configured to modify flow of blood or any body fluid to a tissue. Generally, a device as described herein comprises a flow modifying implant configured for deployment within a blood vessel or other body fluid channel. Generally, a flow modifying implant as described herein comprises a lumen through which blood flows or fluid flows when the flow modifying implant is deployed. A flow modifying device as described herein may be delivered to a target location intravascularly or otherwise minimally invasively.

A flow modifying implant as described herein comprises a body. Optionally, in any example of a flow modifying implant, the implant comprises a tubular body. However, it should be understood that in any example, a flow modifying implant as described herein may comprise any shape including a cylindrical shape, frustoconical shape, a toroidal shape, an elliptical shape, and a cuboidal shape.

Generally, a body of a flow modifying implant as described herein comprises a tubular body that comprises a lumen within it that is configured to allow blood flow or other body fluids to pass through the hollow portion of the body (referred to as a "hollow tubular body" herein). More specifically, the hollow portion of the hollow tubular body is configured to allow the blood or other body fluid to flow through the flow modifying implant.

Optionally, in any example, the hollow tubular body has a cross-sectional diameter along its length. Optionally, in any example, the hollow tubular body has a cross-section that may be circular or elliptical. Optionally, in any example, the cross-sectional diameter of the hollow tubular body is uniform along the length of the hollow tubular body. Optionally, in any example, the hollow tubular body tapers along its length, from an upstream portion to a downstream portion, so that the hollow tubular body does not have a uniform cross-sectional diameter along its length. Optionally, in any example, a hollow tubular body has an inner diameter and an outer diameter that are different. In any of these examples, the outer diameter is uniform along the length of the hollow tubular body and an inner diameter may vary over the length of the hollow tubular body.

A flow modifying implant as described herein comprises a wall. Generally, a hollow portion of a hollow tubular body as described herein is enclosed by one or more walls. Optionally, in any example, a hollow tubular body comprises a single wall that forms a hollow portion within it.

A wall, optionally, in any example, comprises a single material that is uniform in its properties. Optionally, in any example, a wall comprises multiple materials that are uniform in their respective properties relative to each other. Optionally, in any example, a wall comprises a single material comprising different properties. Optionally, in any example, a wall comprises multiple materials each having a different property with respect to each other. Optionally, in any example, wall properties may include but are not limited to porosity, tensile strength, elasticity, or flexibility, as well as other properties known in the art.

A material that forms a wall of a hollow tubular body of a flow modifying implants, optionally, in any example, may be porous to blood or other body fluids, or it may not be porous to blood or other body fluids. Optionally, in any example, a material that forms a wall has the property of being semi-porous. Optionally, in any example, a material that forms a wall has the property of being non-porous. Optionally, in any example, a material that forms a wall includes sections or gradients that are one of porous, semi-porous, and non-porous so that the material has multiple properties. It should be understood that in any of these examples, a material forming a wall may itself comprise multiple other materials.

A material that forms a wall of a hollow tubular body of a flow modifying implant, optionally, in any example, may comprise a polymer, a xenograft, bovine tissue, porcine tissue, a cadaveric human tissue, metals such as titanium material, steel, iron alloy, a chromium alloy, stainless-steel, cobalt alloy, chromium alloy material. Optionally, in any example, a material comprises a cobalt and chromium alloy, nickel alloy, titanium alloy, or Nitinol. In any example, the material may comprise a mesh which may be either from tissue, metals, polymers, or other synthetic materials.

In any example, the wall (or walls) of a hollow tubular body of a flow modifying implant may be compressible relative to an anchoring element of the implant that is configured to provide a rigid support to the flow modifying implant and is at least more resistant to compression than the wall (or walls) of the flow modifying implant.

The hollow tubular body has a first end and second end. Optionally, in any example, a hollow tubular body is configured to taper from the first end of the hollow tubular body to the second end along the length of the flow modifying implant.

Optionally, in any example, a flow modifying implant comprises a ring. Generally, a ring is positioned along the length of the flow modifying implant with respect to the hollow tubular body so that it provides support to the hollow tubular body, including the walls of the hollow tubular body, which are generally more compressible than the ring. In this way, optionally, in any example, the ring may be the only support member in the device. Optionally, in any example, a hollow tubular body comprises more than one ring.

Optionally, in any example, a ring is positioned at a first end of an implant with a tapering hollow body (may be at the widest end of the tapering hollow body, which could be the inflow end or the outflow end. Optionally, in any example, a ring is positioned at a second end of an implant with a tapering hollow body (may be at the narrowest end of the tapering hollow body) which may be the inflow or outflow end. Optionally, in any example, a ring is positioned between a first end and a second end of an implant with a tapering hollow body (may be at some location between the widest and narrowest portion of the tubular hollow body). Optionally, in any example, a ring is coupled to but separate from a wall (or walls) of a hollow tubular body. Optionally, in any example, a ring is integrated with a wall (or walls) of a hollow tubular structure. In these examples, a ring is, for example, integrated in that it is formed of the same material of the wall of the hollow tubular body, and the ring may be more rigid than the wall. Optionally, in any example, a ring is enclosed by the material that forms the wall of the hollow tubular body.

Optionally, in any example, a ring is positioned so that it is coaxial to a longitudinal axis of the hollow tubular body. Optionally, in any example, a ring is coaxial with a first or second opening that, optionally, in any example, is coaxial with a longitudinal axis of the hollow tubular implant and, optionally, in any example, may not be coaxial with a longitudinal axis of the hollow tubular body. Optionally, in any example, a ring is positioned on the outside of the hollow tubular body and, optionally, in any example, a ring is positioned on the inside of the hollow tubular body.

Optionally, in any example, a ring is configured to have a collapsed delivery and an expanded deployed configuration. For example, optionally, in any example, in a delivery configuration the ring is compressed for relatively easier intravascular delivery. Optionally, in any example, a ring is self-expanding when changed from its delivery configuration to its deployed configuration. Optionally, in any example, a ring is balloon expandable when changed from its delivery configuration to its deployed configuration.

Optionally, in any example, a ring provides the rigidity of a support and a wall (or walls) of the hollow tubular implant is entirely compressible so that a portion of the wall is flat (i.e. fully compressed or more than 50% compressed) when no blood or other fluid flows through it. This is similar to a "windsock" that has a rigid opening for receiving a flow of air and a flattened body that expands with the flow of air passing through it. Optionally, in any example, blood or other fluid flow through the windsock results in the expansion of the lumen radially until the walls of the flow modifying implant expand fully and may engage the blood vessel wall. Optionally, in any example, the anchoring element holds the flow modifying implant in place within the blood vessel. Optionally, in any example, the anchoring element is a ring or ellipse with a rigidity greater than the lumen.

FIG. 1 is an example of a flow modifying implant 100. In any example, a flow modifying implant 100 comprises a hollow tubular body 118 (having a total length 112) and comprises an expandable/collapsible ring 116 as well as a wall 108. A flow modifying implant may also comprise a first, or upstream, end 102 and a second, or downstream, end 106. As shown, in FIG. 1, a flow modifying implant 100 comprises a first opening 104 at the first end 102 and a second opening at the second end 106. In any example, a ring 116, may be coupled with the hollow tubular body 118. The hollow tubular body 118 may comprise a wall 108 that is formed from any material disclosed herein or otherwise known in the art. Optionally, in any example, the ring 116 is formed from a different material than the material that forms the wall 108. For example, in any example, ring 116 is formed from Nitinol and wall 108 is formed of fabric such as Dacron, or other polyesters, polymers such as PTFE, ePFTE, or polyurethane, or tissue such as a porous, semi-porous or non-porous porcine, bovine or other xenographic material. Optionally, in any example, the ring 116 and a wall 108 are formed of the same material. For example, in any example, the ring 116 is formed of a metal such as nitinol and a wall 108 is formed of a metal like nitinol or titanium (such as, for example, a titanium mesh).

The ring 116, in any example, may be integrated with wall 108 whether, as ring 116 and wall 108 are formed of the same material or, as optionally, in any example, ring 116 and wall 108 are formed of different materials. Optionally, in any example, a material that forms wall 108 extends a length 110 along the hollow tubular body and ring 116 may be coupled to the wall by adhesion, welding, suturing, or other joining techniques known in the art. Optionally, in any example, wall 108 extends the entire length 112 of the hollow tubular body 118 and the material of the wall either includes the material of the ring (where, for example, they are of the same material), encloses (or surrounds) the ring 116, or covers the ring 116.

While FIG. 1 shows ring 116 at the first end 102, it may be positioned at any point along the length 112 of the hollow tubular body 118. Ring 116, in any example, may be positioned at a second end 106. Optionally, in any example, ring 116 may be positioned at a location between a first end 102 and a second end 106. It should be understood (that while not shown in FIG. 1) a hollow tubular body 118, optionally, in any example, may comprise more than one ring 116.

The ring may be self-expanding or balloon expandable. The ring in a collapsed configuration is sized for delivery to the treatment site. Once expanded by self-expansion or by balloon expansion, the ring is expanded into engagement with the vessel wall to anchor the ring and the implant to the vessel or other target treatment tissue. The downstream portion of the implant is free to float in the fluid path, or if it has a ring it may also be anchored into the tissue.

As shown, a hollow tubular body 118 tapers from a first end 102 towards a second end 106 such that the first end has a larger diameter than the opposite second end. Along the length 110, the flow modifying implant 100 is may be more compressible than it is at ring 116, or it may be the same or less compressible. Optionally, in any example, a wall 108 is made of a material that may be porous, semi-porous, or non-porous and extends along the length 110 of the hollow tubular body 118 (the length may include only the length of the tubular body and optionally include the length of the ring). Optionally, in any example, a ring 116 comprises a porous, semi-porous, or non-porous material. Optionally, in any example, ring 116 comprises a mesh. The hollow tubular body may be a porous or non-porous fabric, polymer, or any other material and may be soft and resilient and may float in the fluid stream like a windsock with or without any additional support structure. In any example the tubular body may simply include a tapered tubular fabric frustoconical body coupled to the ring.

Flow modifying implant 100, may be tapered in order to, among other things, to reduce cross-section in the direction of flow, for example, in a coronary sinus. The coronary sinus happens to generally taper along its length from its (generally) widest point at its ostium along its length in an upstream direction (against flow) since the coronary sinus facilitates venous flow. A flow modifying implant 100 is generally compressible in order to, among other things, form a close fit between a part of the implant and a wall of a blood vessel such as, for example, the coronary sinus. That is a flow modifying implant 100 is configured so at least a portion of its tapering length forms a tight contact with a wall of a blood vessel such as, in any example, a coronary sinus, affixing the flow modifying implant 100 into position within the blood vessel. In any example, a second opening of the hollow body 118 (the outflow end) may be configured to be a smaller diameter than the diameter of the blood vessel into which the flow modifying implant is deployed so that blood flow is modified at the second opening by increasing velocity and decreasing pressure, thereby creating a back pressure upstream. The back pressure may direct flow to other anatomical locations that require blood flow such as tissue that is receiving inadequate oxygenated blood flow.

A hollow tubular body may comprise a longitudinal axis 114 in any example. Optionally, a first opening 104 in the hollow tubular body 118 may be coaxial with the longitudinal axis 114 of the hollow tubular body 118 and the ring 116 is coaxial with the first opening 104 (as well as the longitudinal axis 114). Similarly the second opening (the outflow) may also be concentric with the longitudinal axis.

Figure 2:
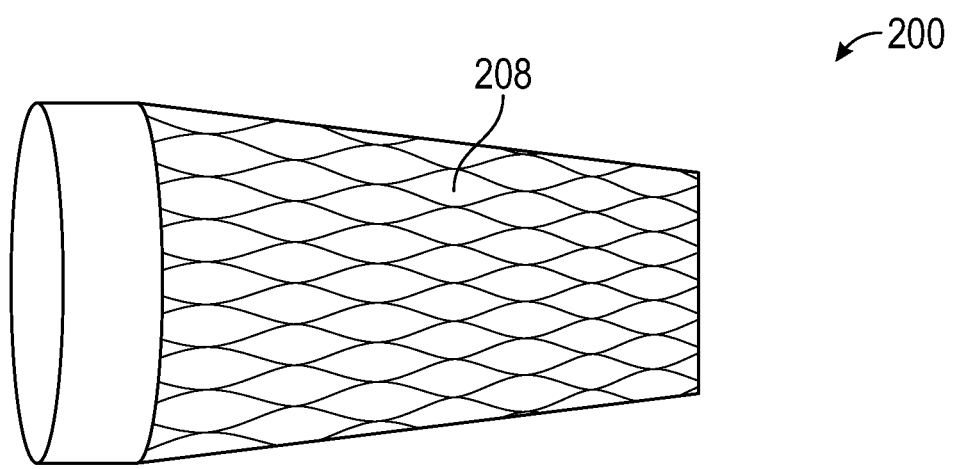
FIG. 2 is a schematic showing a flow modifying implant.

FIG. 2 is any example of a flow modifying implant 200 comprising a hollow tubular body with a mesh wall 208. As shown, a flow modifying implant 200 may comprise a tapered mesh wall 208 configured to provide a porous wall having resistance to blood flow and may be frustoconically shaped. In any example, blood flow is not modified to the same degree through a blood vessel as would be were a non-porous material used instead of the mesh. Endothelialization of the mesh eventually reduces the permeability of the mesh thereby increasing the increase in velocity and decreasing the downstream pressure while increasing the upstream pressure thus enhancing the back pressure at the inflow end which redirects flow to desired areas. In any example, the mesh may also be covered (not illustrated) with a porous or non-porous polymer, fabric or other material to prevent blood from flowing through the porous mesh so the implant has immediate clinical effect as opposed to waiting for endothelialization as described above. Any or all of the tubular body may be covered as desired. The mesh, optionally, in any example, may decrease the incidence of peri-implant thrombus formation. The tubular body may be self-expanding or may be balloon expandable. Closed cells in the tubular body mesh may expand from rectangular or other shaped slots into diamond or other shaped slots upon deployment. The ring may also be balloon expandable or self-expanding and may be a simple annular structure or any other ring-shaped structure. Similarly, the ring expands into engagement with the tissue to anchor the implant. Other aspects of FIG. 2 are generally the same as FIG. 1.

Figure 3:
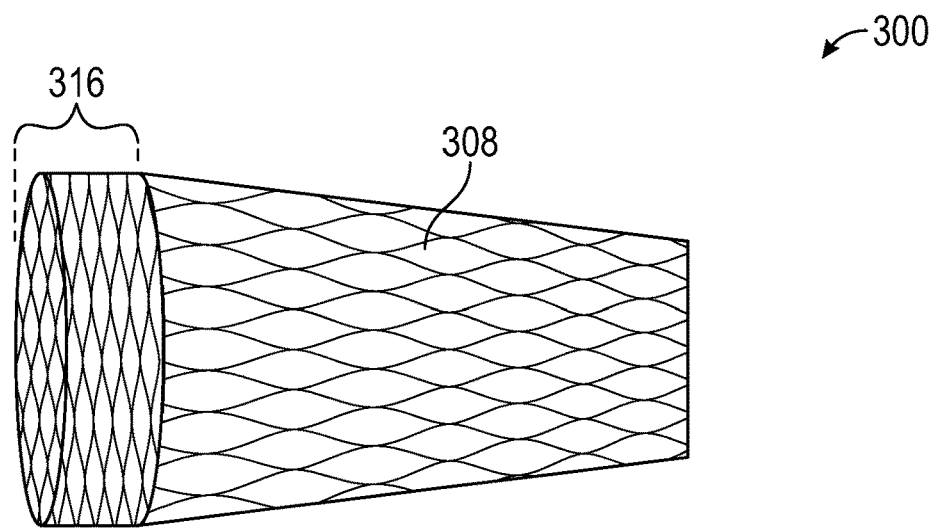
FIG. 3 is a schematic of a flow modifying implant comprising a hollow tubular body with a mesh wall and a ring comprising a mesh.

FIG. 3 shows any example of a flow modifying implant 300 comprising a hollow tubular body with a mesh wall 308 and a ring 316 comprising a mesh. In any example, a ring 316 comprises a more rigid mesh than a mesh of a wall 308, or the ring 316 may be the same or less rigid than the mesh 308. As shown, ring 316, optionally, in any example, comprises a mesh having a different configuration to a mesh of a wall 308. For example, the mesh of a ring 316 has mesh slots, according to any example disclosed herein such as rectangular slots that have a longitudinal axis circumferentially oriented in a collapsed configuration which radially expand into diamond shaped slots with a longitudinal axis that are circumferentially oriented, and these slots are transverse to the closed cell slots of the tubular body. The tubular body has rectangular slots with a longitudinal axis that is generally parallel to the longitudinal axis of the tubular body, and that radially expand into diamond shapes which are similarly axially oriented so that the longitudinal axis of the diamonds are also generally parallel with the longitudinal axis of the tubular body. Optionally, in any example, the mesh of the ring 316 is not aligned with the mesh of a wall 308. Optionally, in any example, a mesh of a ring 316 and a mesh of a wall 308 have identical configurations (not shown). Optionally, in any example, a mesh is plurality of struts interconnected with one another to form diamond shaped closed cells that can be expanded. The ring and tubular body may be balloon expandable or self-expanding, or combinations thereof. Endothelialization of the implant minimizes or prevents fluid flow such as blood flow across the porous mesh and therefore facilitates the reduced flow cross-sectional area of the device which results in increased velocity and lower pressure downstream on the implant with higher pressure and lower velocity upstream of the implant which as previously discussed results in redirected blood flow to desired areas. A cover such as those previously discussed above may be applied to all or a portion of the device including the ring only, the tubular body only, the ring and the tubular body, or portions of the ring and portions of the tubular body thereby reducing or eliminating the need for endothelialization to take effect to create the desired flow dynamics. endothelialization may still be desirable as a uniform monolayer may prevent thrombus formation in this or any example. Other aspects of FIG. 3 generally take the same form as FIGS. 1-2.

Figure 4:
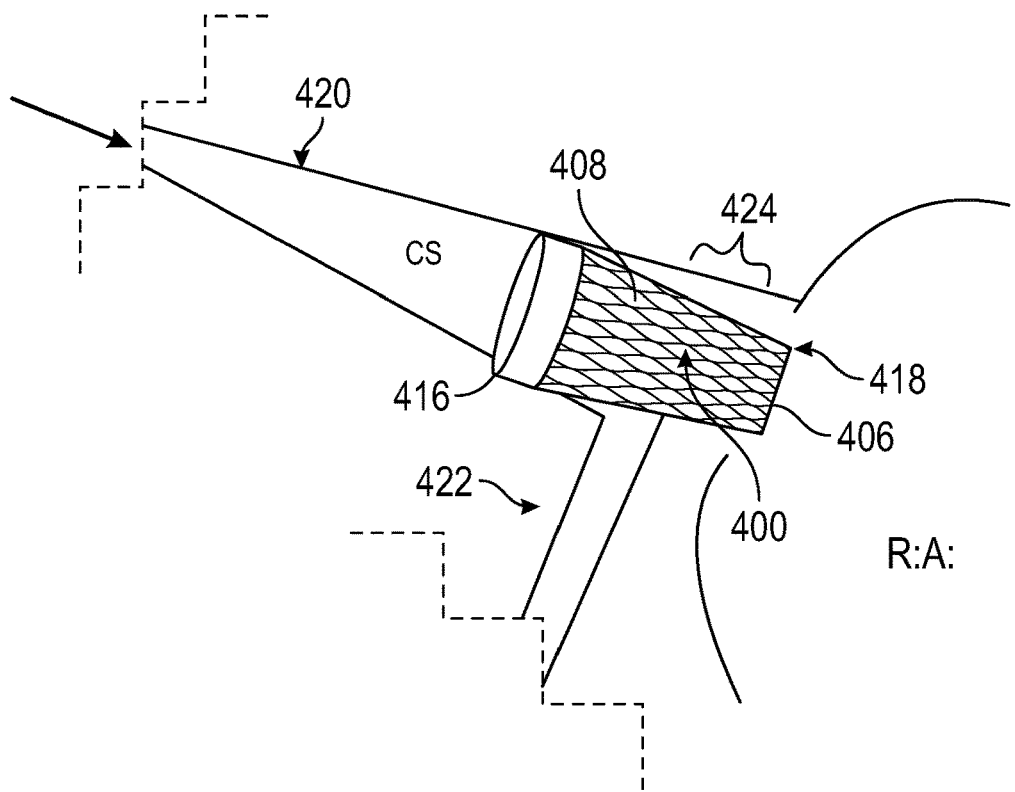
FIG. 4 shows a schematic of a flow modifying implant.

FIG. 4 shows any example of a flow modifying implant 400 being deployed in a blood vessel 420. In any example, a blood vessel 420 may comprise the coronary sinus fluidly coupled with the right atrium of the heart. However, it should be understood that the devices, systems, and methods described herein are suitable for use with any blood vessel including both arteries and veins.

A flow modifying implant 400, according to any example such as FIG. 2, may be deployed within a coronary sinus 420. In any example, the flow modifying implant 400 comprises a tubular body 408 and a ring 416. The body 408 of the implant may be made from a mesh material, or the ring 416 may be made from a mesh material, or the body 408 and the ring 416 may be made from a mesh material. In any example, in its deployed state, implant 400 may be positioned so that the ring 416 is positioned upstream from the ostium 418 of the coronary sinus. The implant 400 tapers so that it has a length 424 that contacts an upstream portion of a wall of the vessel in which it is deployed (here the coronary sinus 420) while the downstream end floats freely in the blood flow stream. Contact with the wall of the coronary sinus 420 (or any other blood vessel) secures the implant in its location within the blood vessel. In any example, only a portion of the implant 400 may come in contact with the wall of the coronary sinus 420 or a vessel. Downstream portions of the implant may or may not engage the vessel wall depending on the taper of the implant or the increase in vessel diameter downstream. In some examples, the ring 416 and/or the wall of the implant may be oversized relative to the size of the vessel in order to ensure that the implant engages the vessel wall and anchors the implant into position. For example, the implant may be oversized up to 10%, 9%, 8%, 7%, 6%, 5%, 4%, 3%, 2%, or 1% relative to the vessel diameter.

Ring 416 may be more rigid than compressible body 408 and both secure the flow modifying implant 400 to its location along the blood vessel 420 and also maintain the patency of the implant so that it can receive blood flow therethrough. The rigidity of ring 416 may allow the implant to rest against the interior of the blood vessel and maintain the implant's position within the vessel through the ring's radial frictional force generated by contacting the interior of the blood vessel. As disclosed above, oversizing may be employed in order to ensure proper anchoring. Optionally, in any example, ring 416 may expand or contract in response to an increase or decrease in blood flow. During or following expansion or contraction, ring 416 remains flush with the interior of the blood vessel and maintains the implant's position within the vessel, again through the use of radial frictional force. In any example, a flow modifying implant 400 tapers to a second end 406 that includes an outflow opening having a smaller diameter than the blood vessel 420 so that blood flow that travels through the flow modifying implant is modified and has a slower velocity and higher pressure at the outflow end than a blood flow would have were the implant not present in the vessel and relative to the inflow end which has lower velocity and higher pressure. As previously disclosed, the ring may be self-expanding or balloon expandable, and the tubular body may be self-expanding or balloon expandable.

A middle cardiac vein 422 may be present and takes off of, or bifurcates, the coronary sinus 420 close to the ostium 418 of the coronary sinus 420. Optionally, in any example, the flow modifying implant 400 is deployed so that it crosses the take-off point of the middle cardiac vein 422 so that the flow modifying implant also functions to modify flow through the middle cardiac vein 422.

Systems and Methods for Delivering and Deploying a Flow Modifying Implant

Described herein are systems and methods that include a flow modifying implant as described herein as a component of the system and method.

In any example, a system may comprise a delivery and deployment device that is configured to deliver and deploy a flow modifying implant as described herein. Optionally, in any example, a delivery and deployment device comprises a catheter with a detachment system. In any example, a flow modifying implant may be coupled to the delivery device in a deployment configuration. Further, in any example, once a delivery location is reached, a detachment system may detach or decouple the flow modifying implant from the delivery and deployment device wherein the flow modifying implant self-expands to deploy or may be balloon or otherwise radially expanded. Optionally, in any example, a detachment system may comprise a plunger or pusher that advances a flow modifying implant out of the lumen of the catheter. Optionally, in any example a detachment system physically detaches a detachable connection between the flow modifying implant and the catheter of the delivery and deployment device. Optionally, in any example, a delivery and deployment device comprises a catheter with a balloon. In any example, a flow modifying implant is delivered to target location in a blood vessel and balloon expanded at the target location.

Figure 5:
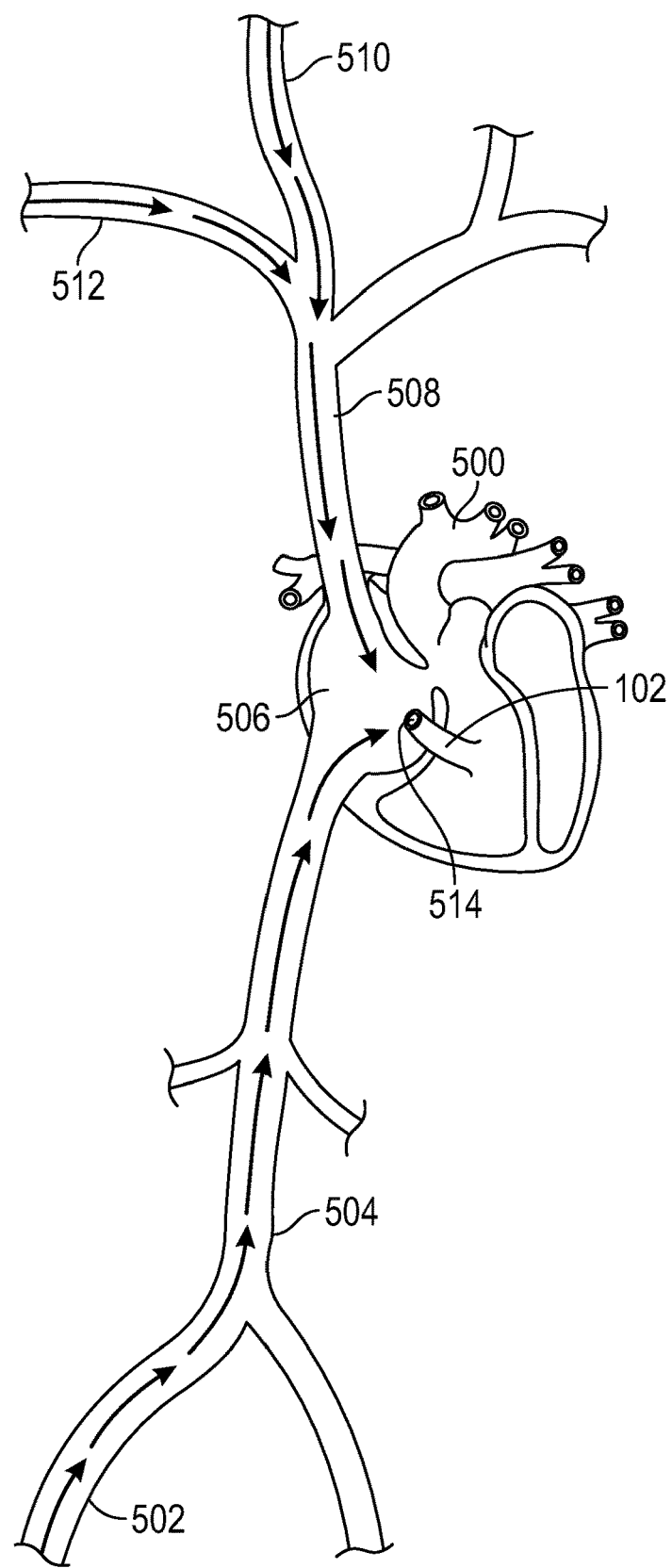
FIG. 5 is a vascular path to a coronary sinus.

FIG. 5 shows a vascular path to coronary sinus 102, which may be used with any example of flow modifying implant and any delivery system. The flow modifying implant 100 may be implanted using a transvascular approach, for example, from the venous system or by crossing through an intra-chamber wall in the heart. In any example of the method, the delivery system is inserted through a jugular vein 510 or a subclavian vein 512 to a right atrium 506 of a heart 500 via a superior vena cava 508 and/or a femoral vein 502, via an inferior vena cava 504. Once in right atrium 506, the delivery system is guided (e.g., through a sharp bend) to an opening 514 into coronary sinus 102. In some patients, a valve exists at the entrance to coronary sinus 102. Antegrade flow through the vascular system back to the heart is shown with arrows in FIG. 5.

Methods for Preventing a Reperfusion Injury with a Flow Modifying Implant

Described herein are methods for preventing a reperfusion injury in a patient using a flow modifying implant. Generally, a reperfusion injury is injury to tissue caused when blood supply is returned to the tissue after a period of ischemia. The ischemia creates a condition wherein restoration of circulation to the tissue results in inflammation and oxidative damage to the tissue. Reperfusion injuries are known to result from angioplasty to open an occluded coronary vessel, especially when performed during an acute myocardial infarction.

Generally, slowing the reperfusion of the ischemic tissue contemporaneously to a revascularization procedure (such as an angioplasty) results in a slowing of blood flow to the ischemic tissue and prevents the acute inflammatory response that causes the reperfusion injury.

Optionally, in any example of the methods described herein, a flow modifying implant comprises a tapering flow modifying implant as described herein and shown in FIGS. 6A-6H and FIGS. 7A-7G. Optionally, in any example, any implant or procedure that modifies flow is suitable for use with the methods described herein. In general, any flow modifying implant disclosed herein may be delivered and deployed at a location proximal to the ischemic tissue and in general that deployment location corresponds to a vessel location that is distal in flow to the occlusion that is opened so that the distal location receives an increased flow of blood from the opening of the occlusion upstream.

Figure 6C:
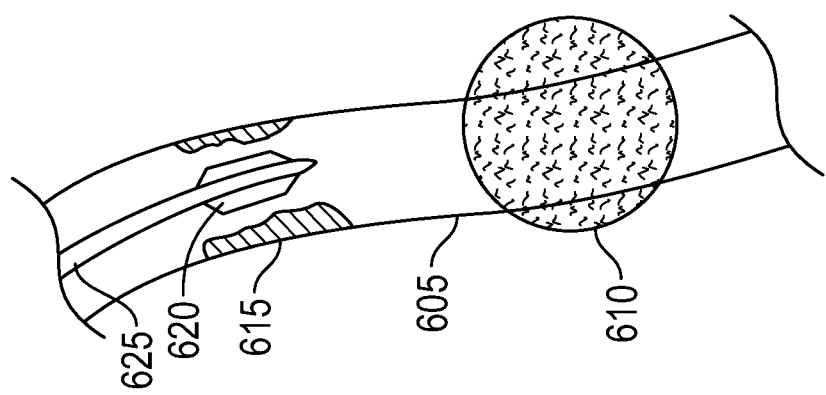
FIGS. 6A-6H illustrate a delivery system and delivery sequence for a flow modifying apparatus and angioplasty procedure.
Figure 6B:
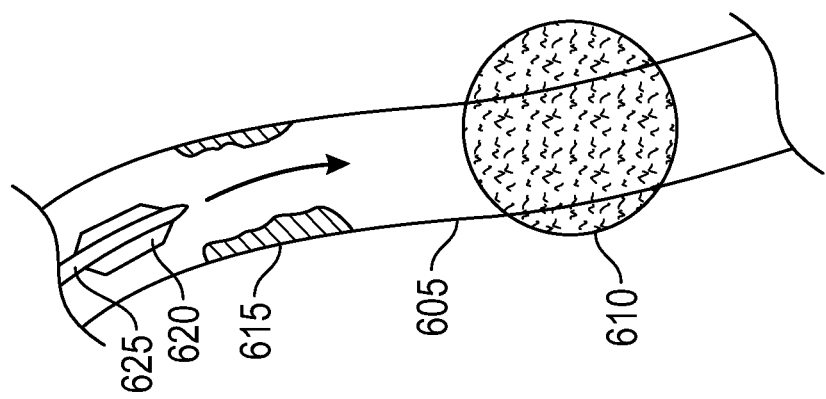
Figure 6A:
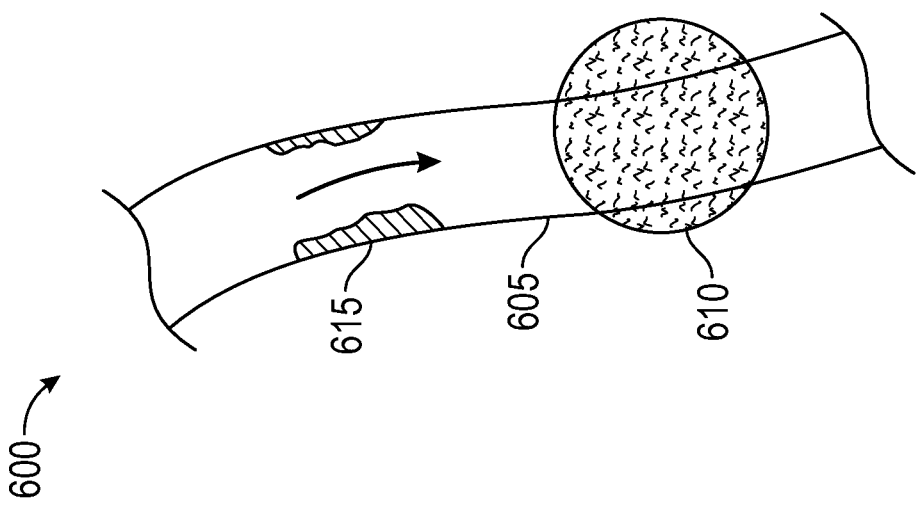

FIGS. 6A-6H illustrate a delivery system and delivery sequence for a flow modifying apparatus and angioplasty procedure. FIG. 6A shows the vasculature of a vessel 600 in which the flow of blood may travel in a blood vessel 605 through a stenotic lesion or other obstruction 615 (e.g. plaque buildup) causing ischemia in tissue region 610 downstream of the stenosis. In any example, a vessel may contain an obstruction followed by ischemic tissue 610 downstream, or a vessel may contain an obstruction 615 without ischemic tissue, or a vessel may not have an obstruction 615, but may have ischemic tissue 610. Rapid revascularization of the obstruction may result in reperfusion injury to the ischemic tissue.

FIG. 6B illustrates a method of treating the ischemic tissue 610 region and performing an angioplasty on the obstruction 615 by inserting a catheter 625 with a radially expandable member 620 such as a balloon into the blood vessel 605. The radially expandable member 620 may be a balloon, a self-expanding member, or mechanically expandable member.

FIG. 6C illustrates the positioning of the catheter 625 with respect to the obstruction 615 in which the radially expandable member 620 may be positioned into the obstructed vessel 605 upstream from the ischemic tissue 610 and adjacent the lesion.

Figure 6F:
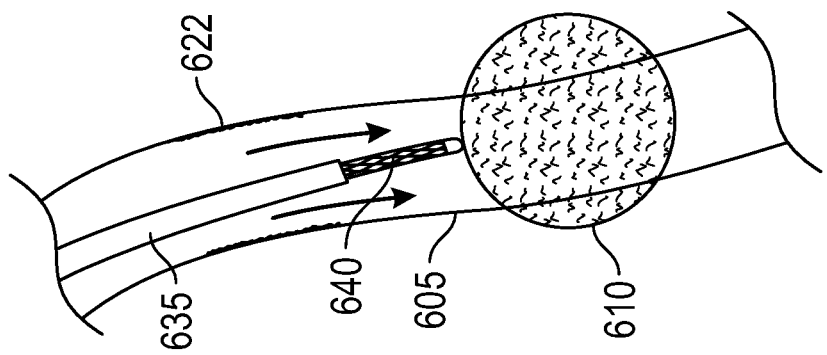
Figure 6E:
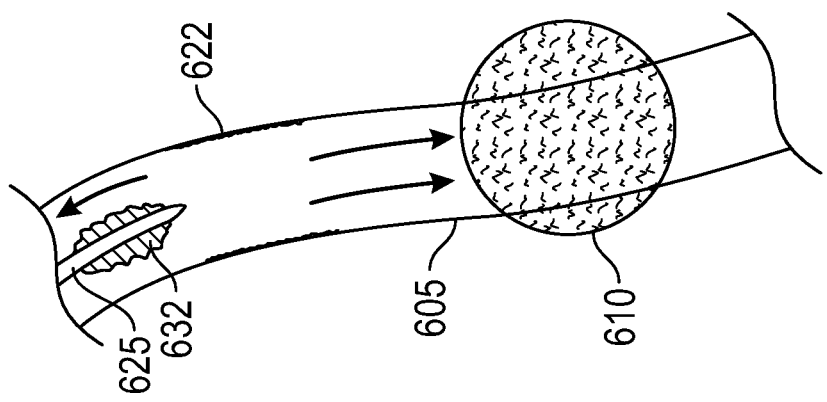
Figure 6D:
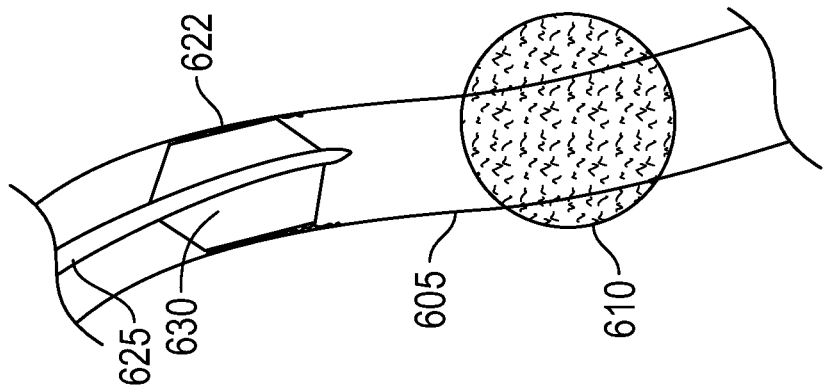

In FIG. 6D, the radially expandable member 630 coupled to the catheter 625 may be expanded to compress the obstruction 622 and allow the blood vessel 605 to open which may allow more blood flow to the ischemic region 610 once the balloon or other expandable member is deflated.

In FIG. 6E, the radially expandable member 632 may be deflated and the catheter 625 may be retracted. The blood vessel 622 may widened which may allow more blood flow to the ischemic tissue 610.

In FIG. 6F, and in any example, after the catheter is retracted, a delivery catheter 635 with a flow modifying implant 640 such as any of those disclosed herein may be introduced into the blood vessel 605. The flow modifying implant 640 may be crimped to the system. The catheter 635 may pass the previous obstruction 622 and introduce the flow modifying implant 640 upstream of the ischemic tissue 610.

Figure 6H:
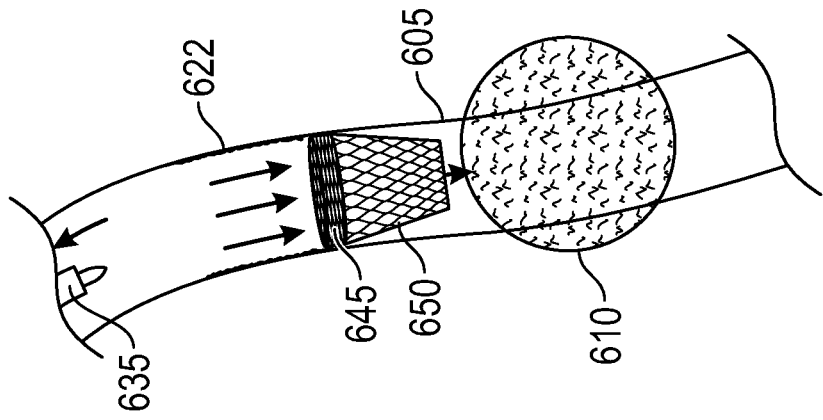
Figure 6G:
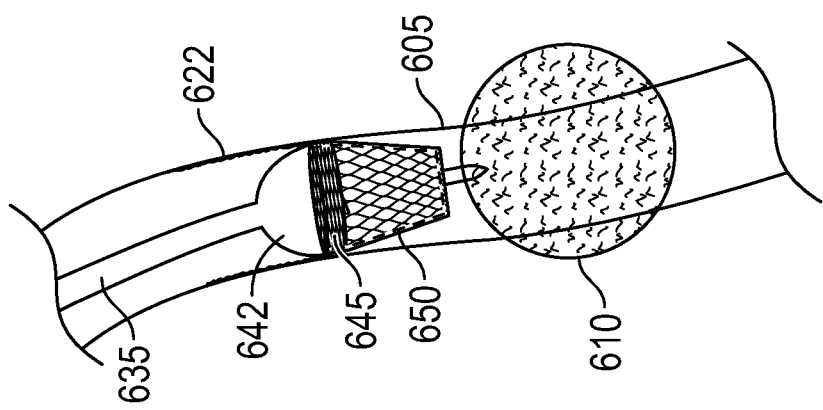

FIG. 6G illustrates the catheter 635 coupled to a radially expandable member 642 such a balloon, that may be disposed underneath the flow modifying implant. The radially expandable member 642 may be expanded which may expand the flow modifying implant. The flow modifying implant may be expanded so that a portion of the implant comes in contact with the wall of the blood vessel 605 upstream of the ischemic tissue. Additionally, or alternatively, the flow modifying implant may be expanded so that the entire surface of the flow modifying implant comes in contact with the wall of the blood vessel 605. In any example, the flow modifying implant may be in a position that is downstream from the previous obstruction 622. Alternatively, or additionally, the flow modifying implant may be positioned to expand in the previously obstructed region. Alternatively, or additionally, the flow modifying implant may be positioned to expand upstream of the obstruction 622. The flow modifying implant may comprise a frustoconical shaped body 650. Alternatively, or additionally, the body 650 may be toroidal, rectangular, elliptical, or any suitable shape thereof. The body 650 may also comprise a mesh that is covered or uncovered. The flow modifying implant may also comprise a ring 645. The ring 645 may be coupled to the body 650 and may be made from a different material or have different properties than the body 650. Alternatively, the ring 645 may be made from the same material or have similar properties to that of the body 650. The body 650 of the flow modifying implant may be expanded before the ring 645, the ring 645 may be expanded before the body 650, or the ring 645 and body 650 may be expanded simultaneously. Expansion of the ring also holds the lumen of the flow modifying implant open and thereby allows a flow of blood to travel therethrough. The implant may be self-expanding in which case retraction of a constraining element such as a sheath allows the device to expand into engagement with the vessel wall and anchor thereto.

In FIG. 6H, the radially expandable member may be deflated, the catheter 635 may be retracted, and the flow modifying implant may remain in the blood vessel 605 to reduce flow velocity and increase pressure at the outflow end and increase pressure and reduce velocity at the inflow end which may redirect flow to desired areas and reduce reperfusion injury downstream. In any example, the flow modifying implant comprises a hollow tubular body 650 having a first end and a second end and tapering from the first end towards the second end in the direction of blood flow or downstream; a first opening at the first end of the hollow tubular body 650 and a second opening at the second end of the hollow tubular body 650, the first opening and the second opening being positioned so that a continuous lumen is formed through the hollow tubular body 650; and a ring 645 positioned at the first end and positioned coaxially with the first opening.

The flow modifying implant may be positioned in the blood vessel so that the ring 645 is upstream of the ischemic tissue 610 and the body 650 and anchors the device in position. The flow modifying implant may have a tapered frustoconical shape which allows for the modification of pressure and velocity of blood as it travels through the flow modifying implant. In any example, the larger diameter of the ring allows for a flow in which exhibits characteristics of having a higher pressure and lower velocity at the inflow end. As the blood flows from the upstream end of the ring 645, towards the downstream end of the body 650, there is a decrease of pressure and an increase in velocity due to the reduced cross-sectional area. The decrease of pressure allows for the blood to move into the ischemic tissue 610 without a "spurt" affect that may result from a high pressure. By lowering the pressure at the outflow region of the flow modifying implant, the flow modifying implant may reduce damage to the tissue as a result of reperfusion injury.

FIGS. 7A-7G shows a similar method as FIGS. 6A-6H but showing a different sequence of performing the angioplasty.

Figure 7B:
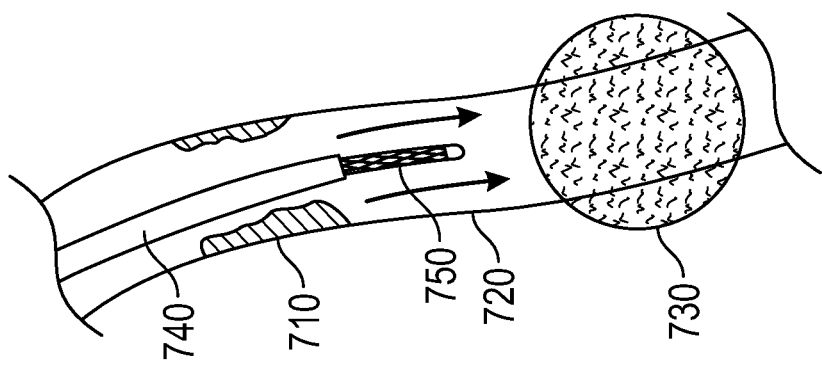
FIGS. 7A-7G illustrate a delivery system and delivery sequence for a flow modifying apparatus and angioplasty procedure.
Figure 7A:
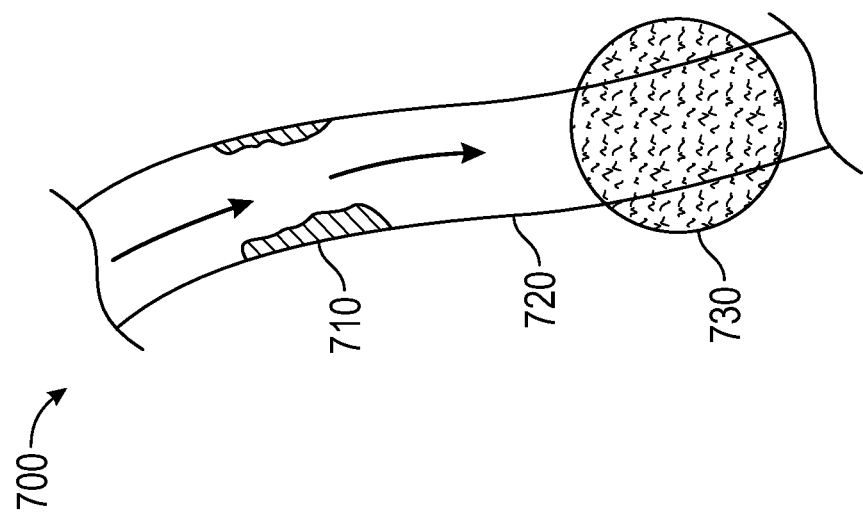

FIG. 7A is a blood vessel similar to that in FIG. 6A showing the flow of blood through an obstruction 710 through the vessel 720 into a region of ischemic tissue 730.

FIG. 7B is the method of delivering a flow modifying implant 750 coupled to a catheter 740 into a blood vessel 720. In FIG. 7B, the flow modifying implant 750 may be delivered into the affected blood vessel 720 before the angioplasty has been performed. In any example, the obstruction 710 may still be causing a reduced blood through the vessel at the time that the flow modifying implant is introduced. The flow modifying implant may be any of those disclosed herein.

Figure 7D:
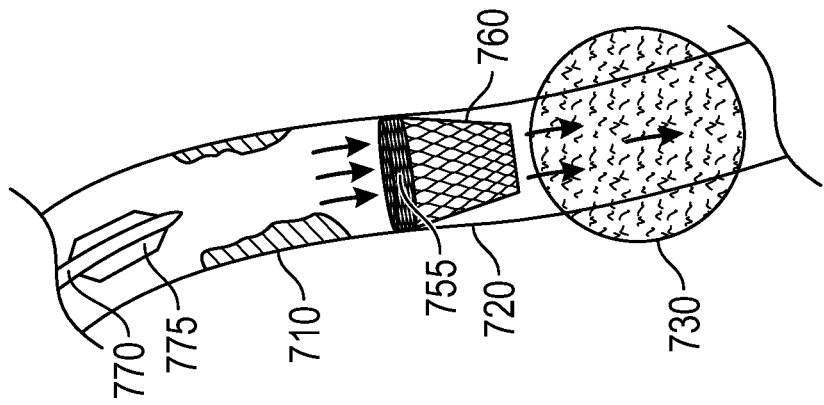
Figure 7C:
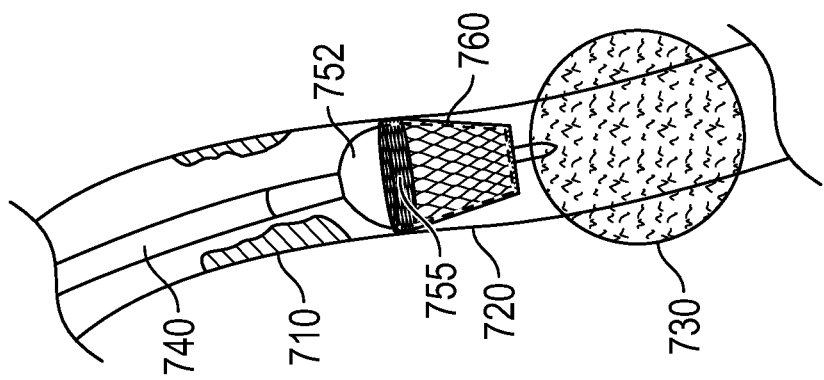

In FIG. 7C, the flow modifying implant is radially expanded. The flow modifying implant may be the same implant as described in FIGS. 6F-6H or any other example disclosed herein, and may comprise a hollow tubular body 760 and a ring 755. The radially expandable member 752 (e.g. a balloon) is expanded as to expand the flow modifying implant. Alternatively, the flow modifying implant may be positioned in the obstruction 710, so that upon expansion, the flow modifying implant is expanded and opens the obstructed vessel 720. In any example, the flow modifying implant may be upstream from the ischemic tissue 730. In any example the implant may be self-expanding and therefore not require a balloon to expand it, although a balloon may optionally be used to tack the implant into position and ensure that the implant is fully expanded.

In FIG. 7D, the flow modifying implant is expanded into engagement with the tissue and modifies blood flow as described in FIG. 6H. In any example, after the flow modifying implant has been delivered to the target region in the blood vessel, a radially expandable member 775 coupled to a catheter 770 (e.g. an angioplasty catheter) may be introduced into the vessel 720. The target region may be upstream the ring 755 and tubular body 760 and the ischemic region 730. Arrows show blood flow through the implant and vessel.

Figure 7G:
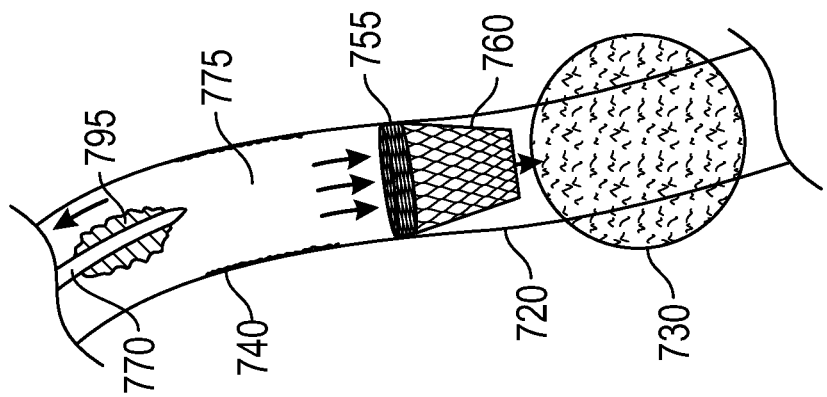
Figure 7F:
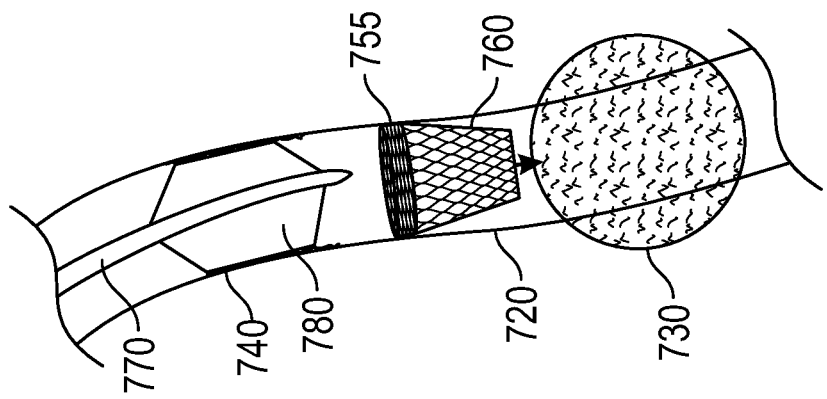
Figure 7E:
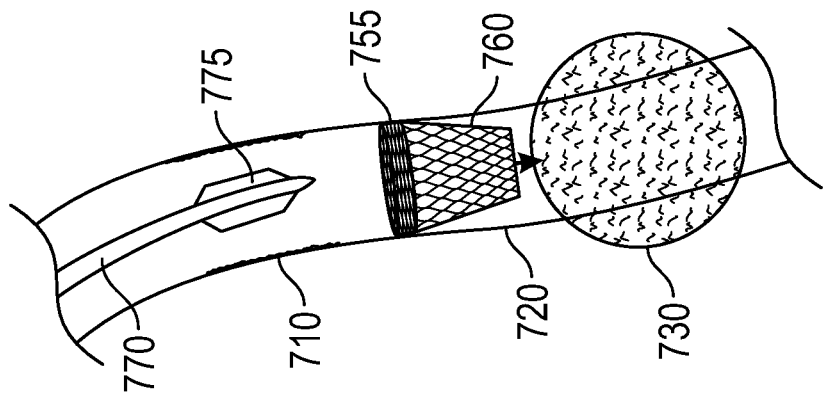

FIG. 7E illustrates the angioplasty catheter being delivered to the stenotic lesion, upstream of the flow modifying implant and the ischemic region 730.

FIG. 7F illustrates expanding the radially expandable member 780 coupled to the catheter 770 into engagement with the stenotic lesion to reduce the plaque using angioplasty techniques known in the art.

In FIG. 7G, the radially expandable member 795 is deflated and the deflated and the catheter 770 is retracted.

FIGS. 8A-8D shows another example of a flow modifying implant. The flow modifying implant may modify or regulate the flow of blood through a vessel.

Figure 8A:
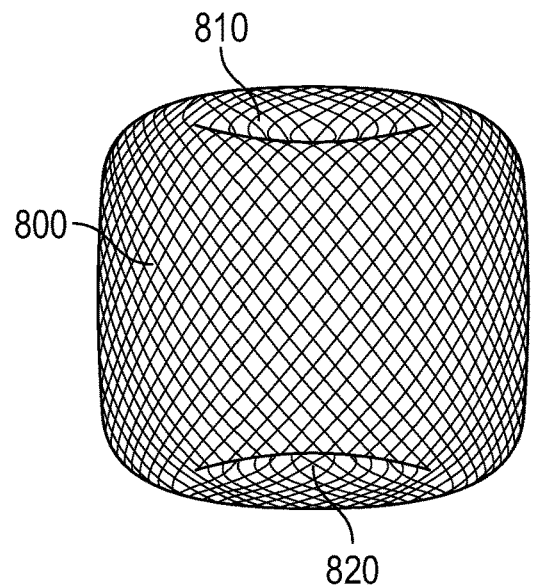
FIGS. 8A-8D illustrate a flow modifying implant.

FIG. 8A illustrates a flow modifying implant comprising hollow tubular body 800 having a first end 810 and a second end 820. The hollow tubular body 800 may be formed from a plurality of braided filaments. The expanded flow modifying implant has a continuous body, wherein the first end 810 may be an invaginated inflow end and the second end 820 may be an invaginated outflow end on the opposite side of the first end 820. The first end 810 and second end 820 may have a lumen extending therethrough. Both inflow and outflow ends may have an arcuate bevel or chamfer leading into the hollow tubular body. The flow modifying implant may have properties of improved radiopacity under imaging to increase accuracy and precision of placement in a vessel. The first end 810, the second end 820, or any portion of the body 800 may comprise of one or more anchoring tabs (not illustrated) that may deploy upon expansion to anchor the flow modifying implant to the blood vessel. Alternatively, the flow modifying implant may anchor to the blood vessel without anchor tabs simply by radially expanding into engagement with the vessel wall. The architecture of the flow modifying implant may allow for the ability to control radial force. The outer surface of the tubular body may be cylindrically shaped and the upper and lower ends of the tubular body may also be chamfered or beveled with a curved corner.

Figure 8B:
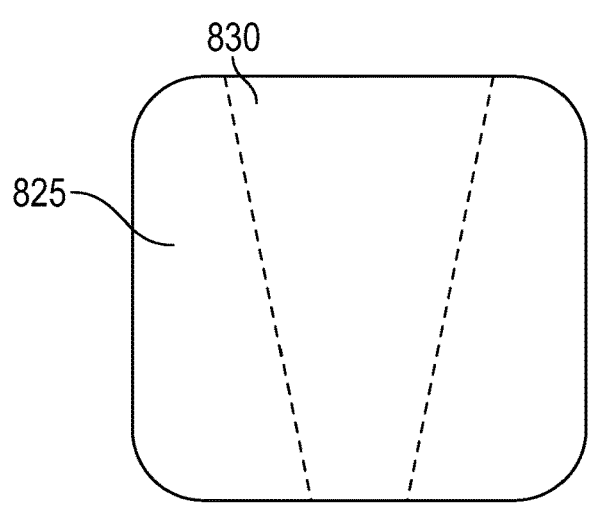

FIG. 8B illustrates the flow modifying implant of FIG. 8A, wherein the lumen 830 may form a linear taper from the first end (inflow end) to the second end (outflow end). The linear taper may be a decreasing taper, or an increasing taper. The body wall 825 of the flow modifying implant therefore may become increasingly thicker, or increasingly thinner depending on the direction of the taper.

Figure 8C:
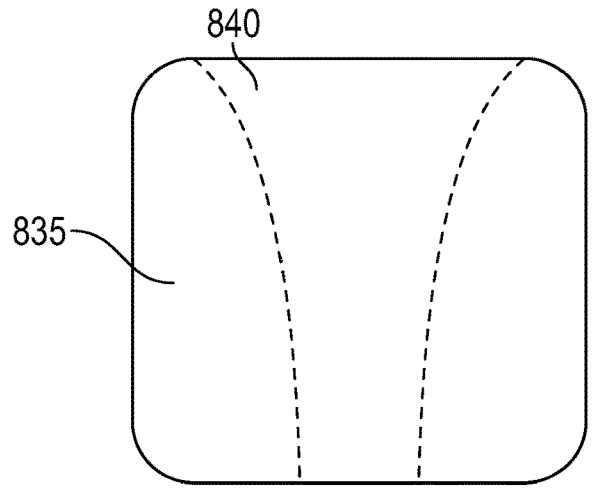

FIG. 8C illustrates the flow modifying implant of FIG. 8A, wherein the lumen 840 may form an arcuate taper from the first end to the second end. The body wall 835 of the flow modifying implant therefore may become increasingly thicker, or increasingly thinner depending on the shape and direction of the arcuate taper.

Figure 8D:
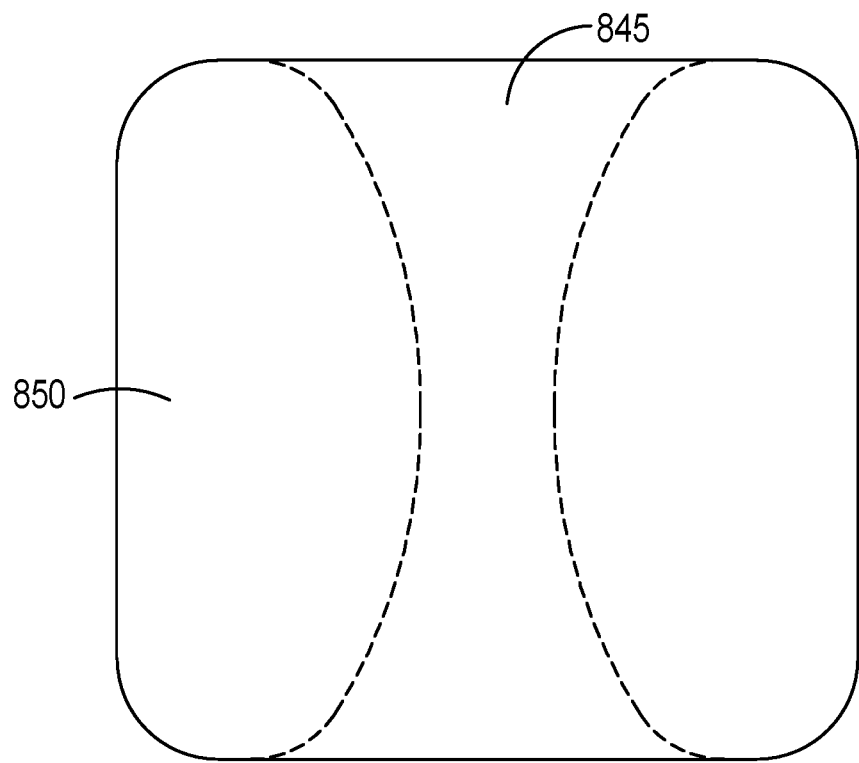

FIG. 8D illustrates the flow modifying implant of FIG. 8A, wherein the lumen 845 may be arcuate with the lumen having a concave shaped wall with the concavity facing radially outward, from the first end to the second end such that the inflow end (first end) is flared, and the outflow end (second end) is flared, and a middle portion between the first and second ends has a smaller diameter than the inflow end or the outflow end. FIG. 8D shows that the body wall 850 of the flow modifying implant therefore may become increasingly thicker from the inflow end until reaching the middle portion and upon reaching the middle portion, the wall becomes increasingly thinner until reaching the outflow end. The shape of the lumen may be an hour glass, a hyperbolic-like curve, or any other reasonable shape of curvature. In this or any example, the filaments will provide increased resistance to blood flow through the sidewall of the implant and that may result in some immediate clinical effect but further endothelialization as previously discussed will help minimize blood flow through the side wall so the implant may modify flow as desired. Also, in this or any example, a cover such as Dacron polyester, PTFE, ePTFE or any polymer may be applied to the outer or inner or both surfaces of the implant to prevent fluid flow across the implant wall thereby avoiding the time required for endothelialization and providing desired fluid flow properties immediately upon implantation and deployment.

Figure 9A:
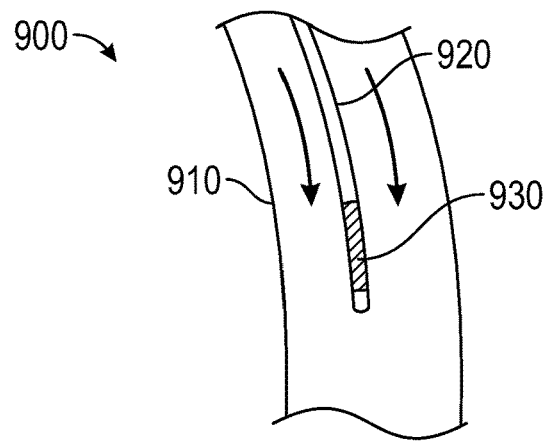
FIGS. 9A-9C illustrate a delivery system and delivery sequence for a flow modifying implant.
Figure 9B:
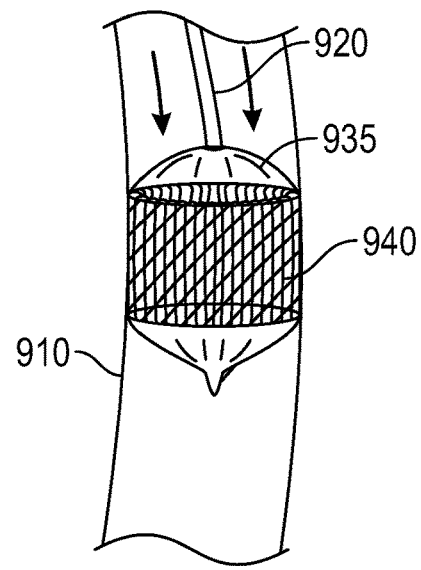
Figure 9C:
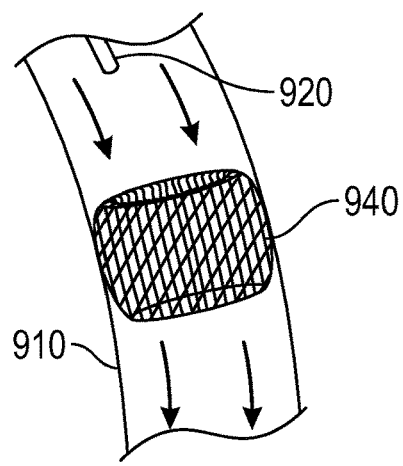

FIG. 9A-9C illustrates the deployment of the flow modifying implant of FIG. 8A.

FIG. 9A illustrates the insertion of a flow modifying implant 930 coupled to a catheter 920 into a blood vessel 910, using any implant disclosed herein.

In FIG. 9B, the flow modifying implant 940 is expanded by expanding a radially expandable member 930 such as a balloon, disposed on the inside surface of the flow modifying implant and coupled to the catheter 920, or it may be self-expanded without the balloon, or a balloon may be used to tack the implant into position and to help full expand the implant. In any example, upon expanding the flow modifying implant 940, a portion of the flow modifying implant 940 may come in contact with the blood vessel and anchor the flow modifying implant. Alternatively, in any example, upon expanding the flow modifying implant, the entire flow modifying implant 940 may come in contact with the blood vessel and anchor the flow modifying implant.

FIG. 9C illustrates the flow modifying implant 940 of FIG. 9A deployed into a desired position. The balloon is deflated and catheter 920 is retracted from the blood vessel 910, and the flow modifying implant 940 remains anchored in the blood vessel.

FIGS. 10A-10F illustrate various delivery systems for any of the flow modifying implants discussed herein. The various delivery systems discussed herein may be balloon expandable, mechanically expandable, or expandable by other means. In any example, a delivery system may be independent from balloons and instead comprise an outer shaft, inner shaft, and a plurality of struts coupled to the inner and outer shafts. In any example, by compressing the struts, the struts are forced to bow radially outward due to the actuation of the inner and outer shafts relative to one another, thereby expanding the flow modifying implant which may b mounted over the struts and causing it to come into engagement with a wall of a vessel.

Figure 10A:
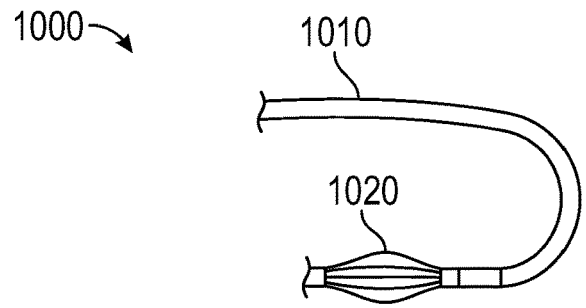
FIGS. 10A-10F illustrate delivery systems for a flow modifying apparatus.

FIG. 10A illustrates a delivery system for a flow modifying implant comprising a single radially expandable head 1020 in the collapsed position, coupled to an outer catheter shaft 1010 and an inner shaft.

Figure 10B:
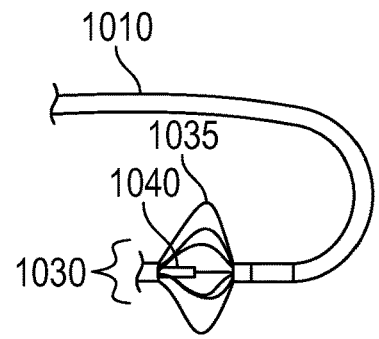

FIG. 10B is the delivery system of FIG. 10A in the expanded configuration. In any example, in the expanded configuration, the plurality of struts 1035 are compressed by relative movement of the inner shaft to the outer shaft, which force them to bow radially outward. The inner shaft 1040 can be seen in which the struts may be coupled thereto, or captured between the inner shaft 1040 and the outer catheter shaft 1010, with the opposite ends of the struts coupled to the outer catheter shaft 1010. The bowed struts 1035 form a bulbous portion 1030 which can be used to expand a flow modifying implant that may be disposed on the outside of the bowed struts 1035.

FIGS. 10C-10F are other examples of delivery systems for any of the flow reducing implants discussed herein. The delivery systems may have one or more expandable strut portions. In any example, the delivery system may comprise two or more bulbous regions. In any example, the bulbous regions are separated by a portion of an outer tube that has a smaller diameter to that of the bulbous portions in their deflated state. Alternatively or additionally, in any example, the bulbous regions are separated by a portion of an outer tube that has a smaller diameter to that of the bulbous regions in their inflated state.

Figure 10C:
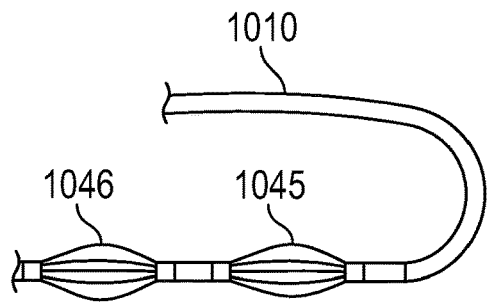

FIG. 10C illustrates a multiple bulbous system comprising a first deflated bulbous portion 1046 and a second deflated bulbous portion 1045 coupled to a catheter 1010, both formed from a plurality of struts.

Figure 10D:
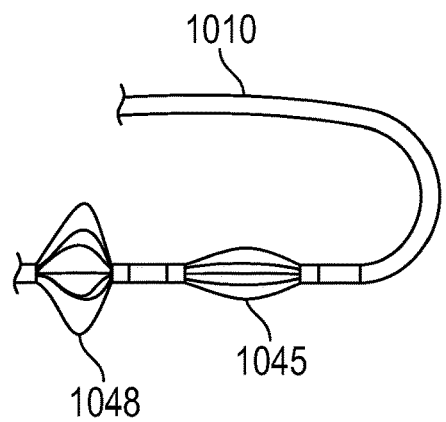

FIG. 10D is the multiple bulbous system of FIG. 10C, wherein the first deflated bulbous portion is inflated and becomes a first inflated bulbous portion 1048 before the second deflated bulbous portion 1045.

Figure 10E:
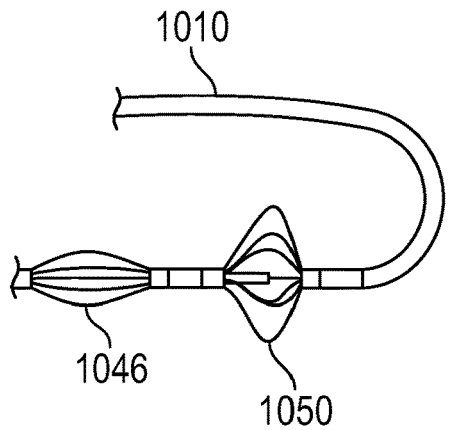

FIG. 10E is the multiple bulbous system of FIG. 10C, wherein the second deflated bulbous portion is inflated and becomes a first inflated bulbous portion 1050 before the first deflated bulbous portion 1046.

Figure 10F:
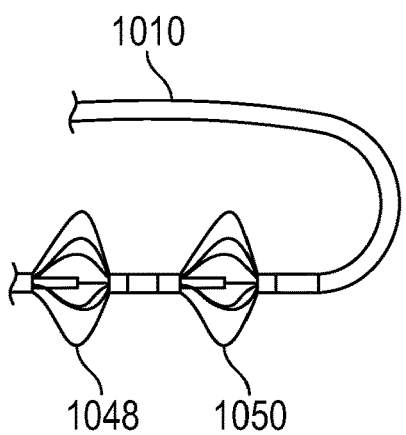

FIG. 10F if the multiple bulbous system of FIG. 10C, in which the first and second deflated bulbous portions are expanded simultaneously to become a first inflated bulbous portion 1048 and a second inflated bulbous portion 1050.

Figure 11A:
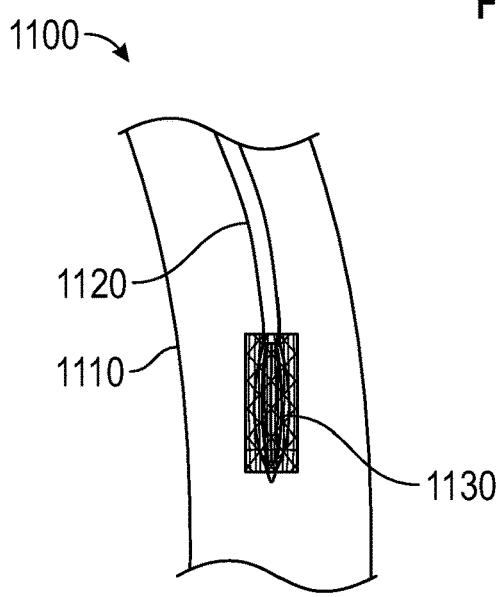
FIGS. 11A-11C illustrate a delivery system and delivery sequence for a flow modifying apparatus.
Figure 11B:
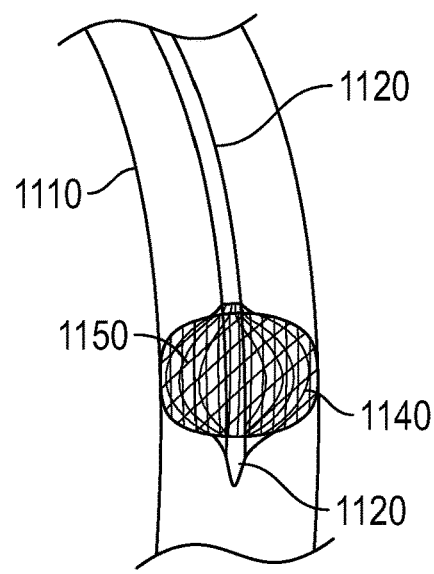
Figure 11C:
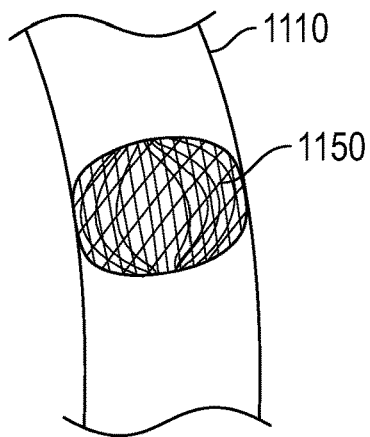

FIGS. 11A-11C illustrate the delivery system of FIGS. 10A-10B in a single bulbous system. FIG. 11A illustrates a catheter 1120 which may be introduced into the delivery site in the blood vessel 1110. A flow modifying implant 1130 such as any of those disclosed herein, is coupled to the catheter 1120. In FIG. 11B, the struts which are coupled to the outer shaft 1120 are compressed and bow radially outward forming a single bulbous region 1140. The bulbous region 1140 forces the flow modifying implant 1150 to expand outward and anchor to the vessel walls 1110. FIG. 11C illustrates the flow modifying implant in the blood vessel after the catheter has been withdrawn from the vessel.

Figure 12A:
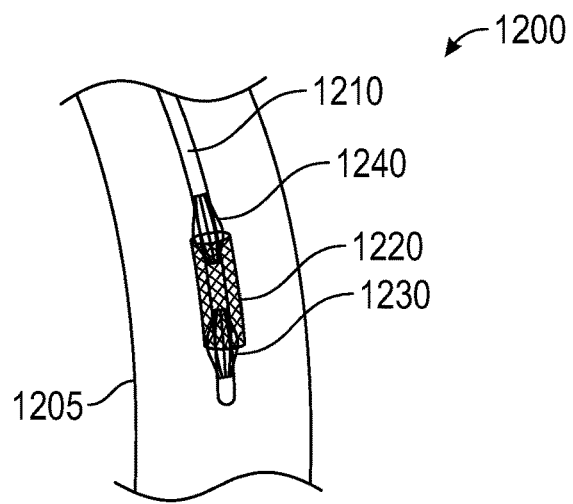
FIGS. 12A-12B illustrate a delivery system and delivery sequence for a flow modifying apparatus.
Figure 12B:
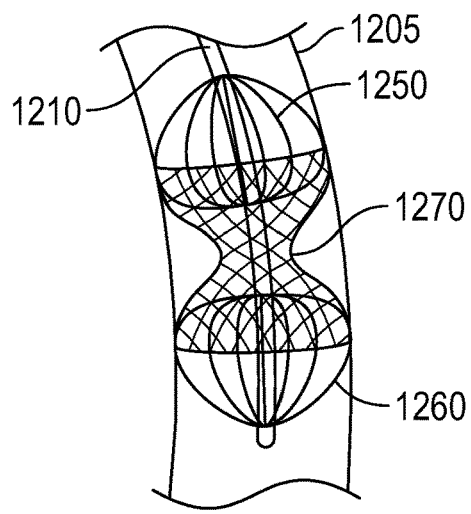

FIGS. 12A-12B illustrate the delivery system of any of the delivery systems of FIGS. 10C-10F. In FIG. 12A, a catheter 1210 is introduced into blood vessel 1205. Optionally, coupled to the catheter may be a first bulbous portion 1230 and a second bulbous region 1240. In any example, the flow reducing implant may be any of those disclosed herein, and may be disposed over a portion in between the first bulbous portion 1230 and the second bulbous portion 1240. In any example, the flow reducing implant may be disposed over the entirety of the first bulbous portion 1230 and the second bulbous portion 1240. FIG. 12B illustrates the delivery system of FIG. 12A in an expanded state. The first bulbous region 1260 may expand a first portion of the flow modifying implant, and the second bulbous region 1250 may expand a second portion of the flow modifying implant, while a middle portion 1270 between the first bulbous portion 1260 and the second bulbous portion 1250 remains unexpanded or only partially expanded to form an hour glass shaped implant. In any example discussed herein, middle portion 1270 remains unexpanded or only partially expanded while one or more flares on either end may be expanded into engagement with the vessel walls to anchor the device. A typical coronary sinus may be 4 mm to 16 mm in diameter, therefore the flared ends of the implant may be expanded approximately 4 mm to 16 mm in diameter, although this is not intended to be limiting. The flared ends may be expanded to any size to engage and anchor the implant into the treatment area tissue. Similarly, the middle portion 1270 may have a diameter approximately 2 mm-4 mm in diameter in order to provide desired flow characteristics, although this is not intended to be limiting. Therefore, upon expansion, the middle portion 1270 may have a diameter 10%-50%, or 15%-45%, or 20%-40%, or 25%-35% of the flare diameter, although this is not intended to be limiting. In any example the narrow section maybe 15%, 20%, 25%, 30%, 35%, 40%, or 45% of the flared diameter, although this is not intended to be limiting.

While examples of the present invention have been shown and described herein, it will be obvious to those skilled in the art that such examples are provided by way of example only. Numerous variations, changes, and substitutions will now occur to those skilled in the art without departing from the invention. It should be understood that various alternatives to the examples of the invention described herein may be employed in practicing the invention. It is intended that the following claims define the scope of the invention and that methods and structures within the scope of these claims and their equivalents be covered thereby.

NOTES AND EXAMPLES

The following, non-limiting examples, detail certain aspects of the present subject matter to solve the challenges and provide the benefits discussed herein, among others.

Example 1 is a flow modifying implant that modifies a flow of blood in a vessel when deployed, the flow modifying implant comprising: a hollow tubular body having a first end and a second end and tapering from the first end towards the second end; a first opening at the first end of the hollow tubular body and a second opening at the second end of the hollow tubular body, the first opening and the second opening being positioned so that a continuous lumen is formed through the hollow tubular body; and a ring positioned at the first end and positioned coaxially with the first opening.

Example 2 is the flow modifying implant of Example 1, wherein a wall of the hollow tubular body comprises a non-porous material.

Example 3 is any of the flow modifying implants of Examples 1-2, wherein a wall of the hollow tubular body comprises a porous material.

Example 4 is any of the flow modifying implants of Examples 1-3, wherein a wall of the hollow tubular body comprises a material having a porosity that varies throughout the material.

Example 5 is any of the flow modifying implants of Examples 1-4, wherein a wall of the hollow tubular body comprises a xenogaft material.

Example 6 is any of the flow modifying implants of Examples 1-5, wherein a wall of the hollow tubular body comprises a porcine or bovine material.

Example 7 is any of the flow modifying implants of Examples 1-6, wherein a wall of the hollow tubular body comprises a polymer or a metal.

Example 8 is any of the flow modifying implants of Examples 1-7, wherein the flow modifying implant is configured to conform to the tapering of a blood vessel so that when deployed in the blood vessel, a portion of a wall of the hollow tubular body is flush with the blood vessel.

Example 9 is any of the flow modifying implants of Examples 1-8, wherein the blood vessel is a coronary sinus.

Example 10 is any of the flow modifying implants of Examples 1-9, wherein the hollow tubular body is configured to taper from the first end to the second end so that when the flow modifying implant is deployed within a coronary sinus, the flow of blood through the flow modifying implant is modified.

Example 11 is any of the flow modifying implants of Examples 1-10, wherein the flow of blood through the modifying implant is modified so that a pressure is increased adjacent the first end relative to a position along the taper.

Example 12 is any of the flow modifying implants of Examples 1-11, wherein the flow of blood through the flow modifying implant is modified so that a velocity of the blood is increased at a position along a tapered region of the flow modified implant relative to the first end.

Example 13 is any of the flow modifying implants of Examples 1-12, wherein a diameter of the first opening is at least double a diameter of the second opening.

Example 14 is any of the flow modifying implants of Examples 1-13, wherein the ring comprises a first material, and the hollow tubular body comprises a second material, and wherein the first material is more rigid than the second material.

Example 15 is any of the flow modifying implants of Examples 1-14, wherein the ring comprises a strut, and wherein the hollow tubular body is free of any struts.

Example 16 is any of the flow modifying implants of Examples 1-15, wherein the flow modifying implant is self-expanding or balloon expandable.

Example 17 is a method for modifying a flow of blood in a vessel, the method comprising: deploying a flow modifying implant in a vessel; anchoring the flow modifying implant into the vessel by radially expanding an anchor element into a wall of the vessel; causing the blood to flow through the flow modifying implant such that the flow of blood passes through an inflow end of the flow modifying implant, the inflow end having a larger cross-sectional area than an outflow end of the flow modifying implant; modifying the flow of blood through the flow modifying implant.

Example 18 is the method of Example 17, wherein the deploying comprises positioning the flow modifying implant at an ostium of a coronary sinus.

Example 19 is any of the methods of Examples 17-18, wherein the deploying comprises positioning the flow modifying implant across a portion of a coronary vein.

Example 20 is any of the methods of Examples 17-19, wherein the blood vessel is tapered, and wherein the causing the blood to flow further comprises conforming the flow modifying implant to the taper of the blood vessel, and engaging the flow modifying implant to be flush with a portion of the blood vessel.

Example 21 is any of the methods of Examples 17-20, wherein the blood vessel is a coronary sinus.

Example 22 is any of the methods of Examples 17-21, wherein the flow modifying implant comprises a ring coupled to a hollow tubular body, and wherein anchoring the flow modifying implant comprises radially expanding the ring into engagement with the wall of the blood vessel.

Example 23 is any of the methods of Examples 17-22, wherein deploying the flow modifying implant comprises self-expanding the flow modifying implant.

Example 24 is any of the methods of Examples 17-23, wherein the modifying the blood to flow comprises increasing a pressure adjacent the inflow end of the flow modifying implant relative to a position along a tapered region between the inflow end and the outflow end.

Example 25 is any of the methods of Examples 17-24, wherein the modifying the blood to flow comprises increasing a velocity of the blood flow adjacent a position along a tapered region of the flow modified implant relative to the inflow end.

Example 26 is a method for reducing reperfusion injury, the method comprising: identifying an ischemic tissue region and a stenotic region in a blood vessel; alleviating the stenosis in the stenotic region; deploying a flow modifying implant distal of the stenotic region and proximal to the ischemic tissue; modifying the blood flow to the ischemic tissue; and reducing reperfusion injury to the ischemic tissue.

Example 27 is the method of Example 26, wherein alleviating the stenosis comprises performing angioplasty on the stenotic region.

Example 28 is any of the methods of Examples 26-27, wherein the performing the angioplasty comprises performing the angioplasty during a myocardial infarction.

Example 29 is any of the methods of Examples 26-28, wherein the area of the ischemic tissue comprises myocardium.

Example 30 is any of the methods of Examples 26-29, wherein the modifying the blood flow further comprises reducing pressure of the blood flow adjacent the ischemic tissue.

Example 31 is any of the methods of Examples 26-30, wherein the modifying the blood flow further comprises increasing velocity of the blood flow adjacent the ischemic tissue.

Example 32 is any of the methods of Examples 26-31, wherein the deploying flow modifying implant comprises deploying the flow modifying implant within an hour of alleviating the stenosis.

Example 33 is any of the methods of Examples 26-32, wherein the deploying the flow modifying implant comprises deploying the flow modifying implant concurrently with or following the alleviating the stenosis.

Example 34 is a flow modifying implant that modifies blood flow in a vessel, the flow modifying implant comprising: a plurality of braided filaments forming a substantially cylindrical tubular body having an inflow end, an outflow end, and a tapering lumen therethrough, wherein the plurality of filaments are invaginated in the inflow end to form an inflow aperture, wherein the plurality of filaments are invaginated in the outflow end to form an outflow aperture, and wherein the substantially cylindrical tubular body has an expanded configuration and a collapsed configuration, the collapsed configuration adapted to be delivered to a target treatment site, and the expanded configuration adapted to engage a wall of the vessel.

Example 35 is the flow modifying implant of Example 34, wherein the tapering lumen comprises a linear taper from the inflow end to the outflow end.

Example 36 is any of the flow modifying implants of Examples 34-35, wherein the tapering lumen comprises an arcuate taper from the inflow end to the outflow end.

Example 37 is any of the implants of Examples 34-36, wherein the tapering lumen adjacent the inflow end is flared, and wherein the tapering lumen adjacent the outflow end is flared, and wherein a middle portion of the tapering lumen disposed between the inflow and outflow ends is smaller than the tapering lumen adjacent the inflow or outflow ends.

Example 38 is any of the implants of Examples 34-37, further comprising a cover disposed over a portion of the substantially cylindrical tubular body.

Example 39 is a flow modifying system that modifies blood flow in a vessel, the flow modifying system comprising: the flow modifying implant of any of Examples 1-37; and a delivery catheter that carries the flow modifying implant.

Example 40 is a method for modifying blood flow in a vessel, the method comprising: providing the flow modifying implant, wherein the flow modifying implant is formed from a plurality of braided filaments; radially expanding the flow modifying implant from a collapsed configuration to an expanded configuration, where the flow modifying implant comprises a substantially cylindrical tubular body; forming an invaginated inflow and outflow end on opposite sides of the substantially cylindrical tubular body, and a lumen extending therethrough; and anchoring the flow modifying implant into engagement with a wall of the vessel.

Example 41 is the method of Example 40, wherein the forming the lumen comprises forming a linear taper from the inflow end to the outflow end.

Example 42 is any of the methods of Examples 40-41, wherein the forming the lumen comprises forming an arcuate taper from the inflow end to the outflow end.

Example 43 is any of the methods of Examples 40-42, wherein the tapering lumen adjacent the inflow end is flared, and wherein the tapering lumen adjacent the outflow end is flared, and wherein a middle portion of the tapering lumen disposed between the inflow and outflow ends is smaller than the tapering lumen adjacent the inflow or outflow ends.

Example 44 is a method for delivering a flow modifying implant into a vessel, the method comprising: providing a delivery catheter comprising an outer shaft, inner shaft, a plurality of struts coupled to the inner and outer shafts, and the flow modifying implant disposed on the plurality of struts; actuating the inner shaft relative to the outer shaft; compressing the plurality of struts to cause the plurality of struts to bow radially outward; radially expanding the flow modifying implant into engagement with a wall of the vessel.

Example 45 is the method of Example 44, the compressing further comprises forming a plurality of bulbous regions separated by a region having a diameter less than the bulbous regions.

Example 46 is any of the methods of Examples 44-45, wherein the forming the plurality of bulbous regions form a plurality of flared regions in the flow modifying implant.

Example 47 is a device for delivering a flow modifying implant into a vessel, the device comprising: an outer shaft; inner shaft, the inner shaft slidably disposed in the outer shaft; a plurality of struts coupled to the inner and outer shafts, wherein actuation of the inner shaft relative to the outer shaft compresses the plurality of struts such that the plurality of struts bow radially outward.

Example 48 is the device of Example 47, wherein the plurality of struts in the bowed configuration form a plurality of bulbous regions separated by a region having a diameter less than the bulbous regions.

Example 49 is any of the devices of Examples 47-48, wherein the plurality of bulbous regions are configured to form a plurality of flared regions in the flow modifying implant.

Example 50 is any of the devices of Examples 47-49, wherein the plurality of flared regions are configured to engage a wall of the vessel.

Example 51 is a system for modifying flow in a vessel, the system comprising: the device of any of Examples 47-50; and the flow modifying implant, wherein the flow modifying implant is disposed on the plurality of struts.

In Example 52, the systems, devices, or methods of any one or any combination of Examples 1-51 can optionally be configured such that all elements of options recited are available to use or select from.

The above detailed description includes references to the accompanying drawings, which form a part of the detailed description. The drawings show, by way of illustration, specific examples in which the invention can be practiced. These examples are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The above description is intended to be illustrative, and not restrictive. For example, the above-described examples (or one or more aspects thereof) may be used in combination with each other. Other examples can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a disclosed example. Thus, the following claims are hereby incorporated into the Detailed Description as examples or examples, with each claim standing on its own as a separate example, and it is contemplated that such examples can be combined with each other in various combinations or permutations. The scope of the invention should be determined with reference to the appended claims, along with the full scope of equivalents to which such claims are entitled.

What is claimed is:

1. A flow modifying implant that modifies a flow of blood in a blood vessel when deployed, the said flow modifying implant comprising:
   a hollow tubular body having a first end defining an upstream terminus of the hollow tubular body and a second end defining a downstream terminus of the hollow tubular body and the flow modifying implant, the flow modifying implant continuously tapering in decreasing cross-sectional area from the first end to the second end;
   a first opening at the first end of the hollow tubular body and a second opening at the second end of the hollow tubular body, the first opening and the second opening being positioned so that a continuous lumen is formed through the hollow tubular body, wherein the hollow tubular body is fabricated from a material configured to hold a shape of the continuous lumen in a deployed state regardless of direction of flow of blood; and
   a ring positioned at the first end so as to form an upstream terminus of the flow modifying implant and positioned coaxially with the first opening, the ring being configured for holding the flow modifying implant in place within the blood vessel,
   wherein the flow modifying implant is configured for implantation into the blood vessel for modifying the flow of blood in the blood vessel,
   wherein the ring comprises a strut, and wherein the hollow tubular body is free of any struts.

2. The flow modifying implant of claim 1, wherein a wall of the hollow tubular body comprises a non-porous material.

3. The flow modifying implant of claim 1, wherein a wall of the hollow tubular body comprises a porous material.

4. The flow modifying implant of claim 1, wherein a wall of the hollow tubular body comprises a material having a porosity that varies throughout the material.

5. The flow modifying implant of claim 1, wherein a wall of the hollow tubular body comprises a xenograft material.

6. The flow modifying implant of claim 1, wherein a wall of the hollow tubular body comprises a porcine or bovine material.

7. The flow modifying implant of claim 1, wherein a wall of the hollow tubular body comprises a polymer or a metal.

8. The flow modifying implant of claim 1, wherein the flow modifying implant is configured to conform to the tapering of the blood vessel so that when deployed in the blood vessel, a portion of a wall of the hollow tubular body is flush with the blood vessel.

9. The flow modifying implant of claim 1, wherein the flow modifying implant is configured to modify flow of a coronary sinus comprising the blood vessel.

10. The flow modifying implant of claim 1, wherein the hollow tubular body is configured to taper from the first end to the second end so that when the flow modifying implant is deployed within a coronary sinus, the flow of blood through the flow modifying implant is modified.

11. The flow modifying implant of claim 10, wherein the flow modifying implant is configured so that the flow of blood through the flow modifying implant is modified so that a pressure is increased adjacent the first end relative to a position along the taper.

12. The flow modifying implant of claim 10, wherein the flow modifying implant is configured so that the flow of blood through the flow modifying implant is modified so that a velocity of the blood is increased at a position along a tapered region of the flow modified implant relative to the first end.

13. The flow modifying implant of claim 1, wherein a diameter of the first opening is at least double a diameter of the second opening.

14. The flow modifying implant of claim 1, wherein the ring comprises a first material, and the hollow tubular body comprises a second material, and wherein the first material is more rigid than the second material.

15. The flow modifying implant of claim 1, wherein the flow modifying implant is self-expanding or balloon expandable to the shape of the continuous lumen of the deployed state.

16. The flow modifying implant of claim 1, wherein the hollow tubular body is rigid.

17. The flow modifying implant of claim 1, wherein the hollow tubular body includes a support to facilitate holding of the shape.

18. The flow modifying implant of claim 1, wherein the hollow tubular body includes a plurality of struts.

19. The flow modifying implant of claim 1, wherein the hollow tubular body is fabricated from metal mesh.

20. A flow modifying implant that modifies a flow of blood in a blood vessel when deployed, the said flow modifying implant comprising:

a hollow tubular body having a first end defining an upstream terminus of the hollow tubular body and a second end defining a downstream terminus of the hollow tubular body and the flow modifying implant, the flow modifying implant continuously tapering in decreasing cross-sectional area from the first end to the second end, wherein the hollow tubular body is configured to not collapse in a deployed state;

a first opening at the first end of the hollow tubular body and a second opening at the second end of the hollow tubular body, the first opening and the second opening being positioned so that a continuous lumen is formed through the hollow tubular body; and a ring positioned at the first end so as to form an upstream terminus of the flow modifying implant and positioned coaxially with the first opening, the ring being configured for holding the flow modifying implant in place within the blood vessel, wherein the flow modifying implant is configured for implantation into the blood vessel for modifying the flow of blood in the blood vessel, wherein the ring comprises a strut, and wherein the hollow tubular body is free of any struts.

21. The flow modifying implant of claim 20, wherein a wall of the hollow tubular body comprises a non-porous material.

22. The flow modifying implant of claim 20, wherein a wall of the hollow tubular body comprises a porous material.

23. The flow modifying implant of claim 20, wherein a wall of the hollow tubular body comprises a material having a porosity that varies throughout the material.

24. The flow modifying implant of claim 20, wherein a wall of the hollow tubular body comprises a xenograft material.

25. The flow modifying implant of claim 20, wherein a wall of the hollow tubular body comprises a porcine or bovine material.

26. The flow modifying implant of claim 20, wherein a wall of the hollow tubular body comprises a polymer or a metal.

27. The flow modifying implant of claim 20, wherein the flow modifying implant is configured to conform to the tapering of the blood vessel so that when deployed in the blood vessel, a portion of a wall of the hollow tubular body is flush with the blood vessel.

28. The flow modifying implant of claim 20, wherein the blood vessel is a coronary sinus.

29. The flow modifying implant of claim 20, wherein the hollow tubular body is configured to taper from the first end to the second end so that when the flow modifying implant is deployed within a coronary sinus, the flow of blood through the flow modifying implant is modified.

30. The flow modifying implant of claim 29, wherein the flow modifying implant is configured so that the flow of blood through the flow modifying implant is modified so that a pressure is increased adjacent the first end relative to a position along the taper.

31. The flow modifying implant of claim 29, wherein the flow modifying implant is configured so that the flow of blood through the flow modifying implant is modified so that a velocity of the blood is increased at a position along a tapered region of the flow modified implant relative to the first end.

32. The flow modifying implant of claim 20, wherein a diameter of the first opening is at least double a diameter of the second opening.

33. The flow modifying implant of claim 20, wherein the ring comprises a first material, and the hollow tubular body comprises a second material, and wherein the first material is more rigid than the second material.

34. The flow modifying implant of claim 20, wherein the flow modifying implant is self-expanding or balloon expandable.

35. The flow modifying implant of claim 20, wherein the hollow tubular body is rigid.

36. The flow modifying implant of claim 20, wherein the hollow tubular body includes a support to facilitate holding of the shape.

37. The flow modifying implant of claim 20, wherein the hollow tubular body includes a plurality of struts.

38. The flow modifying implant of claim 20, wherein the hollow tubular body is fabricated from metal mesh.

* * * * *